United States Patent [19]

Ishizaka et al.

[11] Patent Number: 5,077,010

[45] Date of Patent: Dec. 31, 1991

[54] LONG-TEST-FILM CASSETTE FOR BIOCHEMICAL ANALYSIS, AND SYSTEM FOR LOADING THE SAME

[75] Inventors: Hideo Ishizaka, Kanagawa; Yoshio Saito, Saitama; Yukihide Miyata, Kanagawa; Takashi Koizumi, Kanagawa; Yasuhiro Asai, Kanagawa; Shinichi Nakama, Kanagawa; Tadashi Uekusa, Kanagawa; Shinichi Matsuda, Kanagawa; Koichi Yamada, Kanagawa, all of Japan

[73] Assignee: Fuji Photo Film Co., Ltd., Kanagawa, Japan

[21] Appl. No.: 219,011

[22] Filed: Jul. 14, 1988

[30] Foreign Application Priority Data

| Jul. 15, 1987 | [JP] | Japan | 62-176566 |
| Oct. 13, 1987 | [JP] | Japan | 62-258517 |
| Oct. 13, 1987 | [JP] | Japan | 62-258518 |
| Oct. 16, 1987 | [JP] | Japan | 62-261349 |
| Oct. 16, 1987 | [JP] | Japan | 62-261350 |
| Oct. 16, 1987 | [JP] | Japan | 62-261351 |
| Oct. 17, 1987 | [JP] | Japan | 62-262416 |
| Oct. 17, 1987 | [JP] | Japan | 62-262417 |
| Oct. 17, 1987 | [JP] | Japan | 62-262418 |
| Oct. 19, 1987 | [JP] | Japan | 62-264721 |
| Nov. 18, 1987 | [JP] | Japan | 62-291433 |
| Dec. 16, 1987 | [JP] | Japan | 62-318147 |
| Dec. 16, 1987 | [JP] | Japan | 62-318148 |
| Dec. 16, 1987 | [JP] | Japan | 62-318151 |

[51] Int. Cl.⁵ .................. G01N 35/02; G01N 35/04; G01N 21/78
[52] U.S. Cl. ...................... 422/56; 422/58; 422/62; 422/66; 422/102; 422/104
[58] Field of Search ............ 422/56, 57, 58, 62, 422/63, 64, 65, 66, 68.1, 102, 104; 62/132

[56] References Cited

U.S. PATENT DOCUMENTS

| 3,675,488 | 7/1972 | Viktora et al. | 422/66 |
| 3,728,081 | 4/1973 | Bidanset | 259/23 |
| 3,904,369 | 9/1975 | Adler et al. | 422/66 |
| 3,918,910 | 11/1975 | Soya et al. | 422/66 |
| 4,218,421 | 8/1980 | Mack, Jr. et al. | |
| 4,421,719 | 12/1983 | Burleigh | 422/66 |
| 4,924,714 | 5/1990 | Gross | 422/66 |
| 4,954,319 | 9/1990 | Koizumi et al. | 422/66 |
| 4,959,976 | 10/1990 | Matsuda et al. | 422/66 |

FOREIGN PATENT DOCUMENTS

| 0110013 | 6/1984 | European Pat. Off. . |
| 1046547 | 12/1951 | France . |
| 0021677 | 7/1978 | Japan . |
| 0164356 | 12/1980 | Japan . |
| 0077746 | 6/1981 | Japan . |
| 1-134257 | 5/1989 | Japan | 422/82.05 |
| 1-134258 | 5/1989 | Japan | 422/82.05 |
| 1-134260 | 5/1989 | Japan | 422/82.05 |
| 1-134261 | 5/1989 | Japan | 422/82.05 |
| 8505563 | 12/1985 | PCT Int'l Appl. . |

OTHER PUBLICATIONS

European Search Report No. 88 11 1417, Dec. 14, 1988, by examiner S. K. Flintoff.

Primary Examiner—David L. Lacey
Assistant Examiner—Kimberly A. Trautman
Attorney, Agent, or Firm—Sughrue, Mion, Zinn Macpeak & Seas

[57] ABSTRACT

A long-test-film cassette for biochemical analysis comprises an unused film cassette part accommodating an unused long test film for biochemical analysis, and a used film cassette part for accommodating the long test film which has been pulled out of the unused film cassette part and used for biochemical analysis. A leading edge of the film is secured to a reel in the used film cassette part. In a cassette loading system, the unused film cassette part is provided with a protruded test film outlet portion and is loaded to a refrigerating compartment of an analysis apparatus with the test film outlet portion fitted in a hole of the refrigerating compartment.

22 Claims, 27 Drawing Sheets

FIG.43
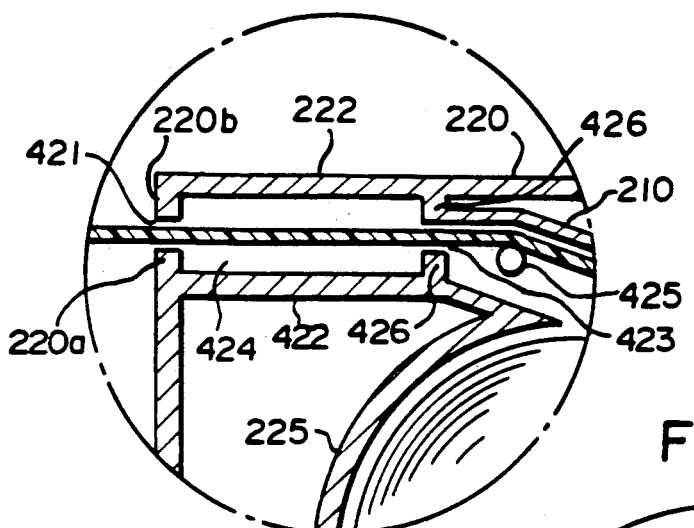
FIG.44
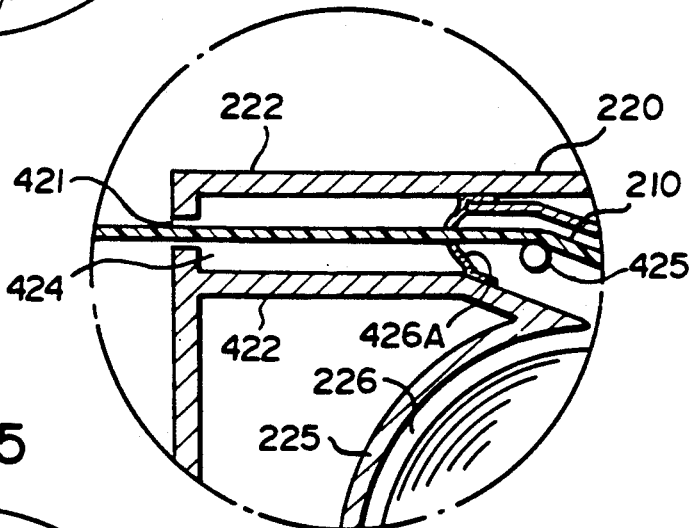
FIG.45

LONG-TEST-FILM CASSETTE FOR BIOCHEMICAL ANALYSIS, AND SYSTEM FOR LOADING THE SAME

BACKGROUND OF THE INVENTION

1. Field of the Invention

This invention relates to a cassette accommodating a long test film, which contains a reagent giving rise to a change in optical density by a reaction with a liquid sample such as urine or blood, for use in a biochemical analysis apparatus for quantitatively determining chemical constituents or physical constituents contained in the liquid sample. This invention also relates to a system for loading the test film cassette.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a liquid sample simply by applying a droplet of the liquid sample. With the chemical analysis slide, it is possible to analyze a liquid sample more simply and more quickly than with the conventional wet type analysis method. Therefore, the use of the chemical analysis slide is desirable particularly in medical organizations, research laboratories, or the like where many samples are to be analyzed.

In order to analyze a chemical constituent or the like contained in a liquid sample by use of the chemical analysis slide, a measured amount of the liquid sample is put on the chemical analysis slide and is maintained at a predetermined temperature (i.e. incubated) for a predetermined time in an incubator to cause a color reaction. The chemical analysis slide is then exposed to measuring light having a wavelength selected in advance in accordance with the combination of the constituent of the liquid sample with a reagent contained in the reagent layer of the chemical analysis slide, and the light reflected by the chemical analysis slide is measured in terms of the optical density. In this manner, it is possible to achieve quantitative analysis of the chemical constituent or the like.

In the medical organizations, research laboratories or the like in which many liquid samples are to be analyzed, it is desirable that the analysis be conducted automatically and sequentially. To satisfy this need, there have been proposed various chemical analysis apparatuses for carrying out sample analysis automatically and sequentially by use of the aforesaid chemical analysis slides. One of such chemical analysis apparatuses is disclosed in, for example, Japanese Unexamined Patent Publication No. 56(1981)-77746. Also, as a means for analyzing liquid samples automatically and sequentially, there has been proposed in, for example, U.S. Pat. No. 3,526,480 an apparatus wherein a long tape-like test film containing a reagent is accommodated instead of the aforesaid chemical analysis slides, and sample application, incubation and measurement are carried out sequentially by pulling out the test film.

With the technique wherein a single chemical analysis slide is used for a single measurement, many chemical analysis slides must be processed for automatically and sequentially carrying out the analysis of liquid samples, and therefore the apparatus becomes complicated, large and expensive. On the other hand, with the technique wherein the long tape-like test film is used, though the measurement can be carried out automatically and sequentially, the long test film is stained by the hands of the operator contacting the long test film at the time the long test film is accommodated in the apparatus, and an error arises with the measurement results. Also, at the time the long test film on which the liquid samples have been applied and which has been used for the measurement is taken out of the apparatus, the hands of the operator contact the long test film and is stained by the liquid samples. On the other hand, after the long test film is accommodated in the apparatus, the unused portion of the long test film on which no liquid sample has yet been applied must be maintained at a predetermined temperature and humidity. Also, it is necessary for the long test film to be adapted to use in various types of apparatuses having different processing capacity.

SUMMARY OF THE INVENTION

The primary object of the present invention is to provide a long-test-film cassette for biochemical analysis which accommodates a long test film so that the long test film is usable in various types of apparatuses and is free of contact with the hands of the operator at the time the long test film is accommodated in and taken out of the apparatus, which is adapted to maintenance of an unused portion of the long test film at a predetermined temperature and humidity.

Another object of the present invention is to provide a long-test-film cassette for biochemical analysis wherein an unused portion of a long test film maintained at a desired low temperature and low humidity is fed to an analysis apparatus without being exposed to a high temperature and high humidity, whereby analysis results are obtained accurately with good reproducibility.

A further object of the present invention is to provide a system for loading a long-test-film cassette for biochemical analysis, which prevents entry of ambient high-temperature, high-humidity air into a refrigerating compartment loaded with an unused film cassette part accommodating an unused portion of the long test film.

A still further object of the present invention is to provide a system for loading a long-test-film cassette for biochemical analysis, wherein an unused portion of a long test film maintained at a desired low temperature and low humidity is fed to an analysis apparatus without being exposed to a high-temperature, high humidity atmosphere, whereby analysis results are obtained accurately with good reproducibility.

The present invention provides a first long-test-film cassette for biochemical analysis comprising:

i) an unused film cassette part accommodating an unused long test film for biochemical analysis, and ii) a used film cassette part provided independently of said unused film cassette part for accommodating said long test film which has been pulled out of said unused film cassette part and used for biochemical analysis.

The present invention also provides a second long-test-film cassette for biochemical analysis comprising:

i) an unused film cassette part accommodating an unused long test film for biochemical analysis in a roll form, and ii) a used film cassette part for winding up and accommodating the used film, which has been used for biochemical analysis, in a roll form, a leading edge of said film being secured to a reel in said used film cassette part, wherein a test film outlet portion of said unused film cassette part has such a configuration that air inside of said unused film cassette part and air outside thereof do not substantially mix with each other naturally.

The present invention further provides a test film cassette loading system for loading an unused film cassette part accommodating an unused long test film for biochemical analysis in a roll form to a refrigerating compartment of a biochemical analysis apparatus, wherein said unused film cassette part is provided with a test film outlet portion having a configuration projected out of a main body of said unused film cassette part, and said refrigerating compartment has a substantially airtight configuration outside of a hole into which said test film outlet portion of said unused film cassette part is to be fitted, whereby said unused film cassette part is loaded to said refrigerating compartment with said test film outlet portion fitted in said hole of said refrigerating compartment.

The present invention still further provides a third long-test-film cassette for biochemical analysis comprising:

i) an unused film cassette part accommodating an unused long test film for biochemical analysis in a roll form, and ii) a used film cassette part for winding up and accommodating the used film, which has been used for biochemical analysis, in a roll form, wherein said unused film cassette part and said used film cassette part are combined integrally with each other so that the space inside of said unused film cassette part and the space inside of said used film cassette part are independent of each other, and a leading edge of said film is secured to a reel in said used film cassette part.

With the first long-test-film cassette for biochemical analysis in accordance with the present invention wherein the unused long test film for biochemical analysis is accommodated in the unused film cassette part and is accommodated in this form in the biochemical analysis apparatus, the long test film can be prevented from contacting the hands of the operator at the time it is accommodated in the apparatus and producing an error in the measurement results. Also, the long test film pulled out of the unused film cassette part and used for biochemical analysis is accommodated in the used film cassette part, and therefore there is no risk of the hands of the operator contacting and being stained by the used long test film on which the liquid sample has already been applied at the time the used long test film is to be taken out of the apparatus. Also, with the first long-test-film cassette for biochemical analysis in accordance with the present invention wherein the unused film cassette part and the used film cassette part are provided independently of each other, the hole of the refrigerating compartment through which the unused long test film is to be pulled out of the refrigerating compartment accommodating the unused long test film and kept at a predetermined temperature and humidity for maintaining the unused long test film at the predetermined temperature and humidity may be as small as the cross-sectional size of the long test film. Therefore, the hole of the refrigerating compartment need not be broadened for the unused film cassette part or the like, and the inside of the refrigerating compartment can be efficiently kept at the predetermined temperature and humidity. Furthermore, with the unused film cassette part and the used film cassette part provided independently of each other, the long test film can be used in various types of apparatuses even though the distance between the position at which the unused film cassette part is accommodated in the apparatus and the position at which the used film cassette part is accommodated in the apparatuses differs among the apparatuses.

With the second long-test-film cassette for biochemical analysis in accordance with the present invention wherein the unused film cassette part is constituted so that air inside of the unused film cassette part and air outside thereof do not substantially mix with each other naturally, the unused portion of the long test film accommodated in the unused film cassette part can be maintained at a low temperature and low humidity without being exposed to ordinary ambient air even though the long-test-film cassette which has been stored at a low temperature and low humidity up to the time of usage is processed in ordinary ambient air for loading to the refrigerating compartment of the analysis apparatus (the processing time is comparatively short). Therefore, the long test film does not deteriorate, and analysis results can be obtained accurately with good reproducibility.

With the test film cassette loading system in accordance with the present invention, it is possible to easily prevent entry of high-temperature, high-humidity ambient air into the refrigerating compartment loaded with unused film cassette part accommodating the unused portion of the long test film. Also, with the test film cassette loading system in accordance with the present invention, the unused portion of the long test film maintained at a desired low temperature and low humidity can be fed to the analysis apparatus without being exposed to a high-temperature, high-humidity atmosphere, and analysis results can be obtained accurately with good reproducibility.

With the third long-test-film cassette for biochemical analysis in accordance with the present invention wherein the unused film cassette part and the used film cassette part are combined integrally with each other, the long-test-film cassette can be loaded quickly to the analysis apparatus by simply adjusting the position of the cassette by a one-touch operation. Also, with the third long-test-film cassette for biochemical analysis in accordance with the present invention wherein the space for accommodating the unused film portion and the space for accommodating the used film portion are separated by a partition, it is also possible to eliminate the problem that the unused film portion is deteriorated by a detrimental gas such as steam produced by the used film portion. Furthermore, with the third long-test-film cassette for biochemical analysis in accordance with the present invention, only the unused portion of the long test film can be efficiently kept cool with the cassette loaded to the analysis apparatus.

BRIEF DESCRIPTION OF THE DRAWINGS

FIG. 12 is used, FIGS. 14A, 14B, 15A, 15B. 16, 17 and 18 are schematic views showing further embodiments of the first long-test-film cassette for biochemical analysis in accordance with the present invention, FIGS. 43, 44, 45 and 46 are enlarged sectional views showing the examples of the configurations of the film outlet portion of the unused film cassette part in the modification shown in FIG. 41.

DESCRIPTION OF THE PREFERRED EMBODIMENTS

The present invention will hereinbelow be described in further detail with reference to the accompanying drawings.

Figure 1:
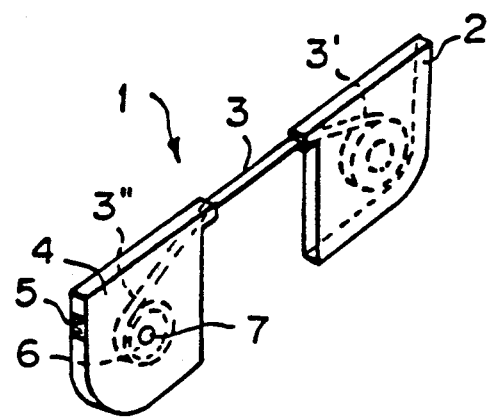
FIG. 1 is a perspective view showing an embodiment of the first long-test-film cassette for biochemical analysis in accordance with the present invention.

With reference to FIG. 1, a long-test-film cassette 1 for biochemical analysis in accordance with the present invention is composed of an unused film cassette part 2, a long test film 3, and a used film cassette part 4. An unused portion 3' of the long test film 3 is wound up and accommodated in the unused film cassette part 2, and a used portion 3" of the long test film 3 is wound up and accommodated in the used film cassette part 4. The lot number, film number, measurement item, working life and other information on the long test film 3 are indicated by, for example, a bar code 5, on one face of the used film cassette part 4. At the center of a reel 6 in the used film cassette part 4, a hole 7 is provided for engagement with a rotation shaft of a motor for pulling the long test film 3 out of the unused film cassette part 2 after the long test film 3 has been accommodated in a biochemical analysis apparatus as will be described later. The long test film 3 is accommodated in the apparatus in the form wound up in the unused film cassette part 2 and the used film cassette part 4. As shown in FIG. 1, the unused film cassette part 2 and the used film cassette part 4 are formed independently of each other.

Figure 2:
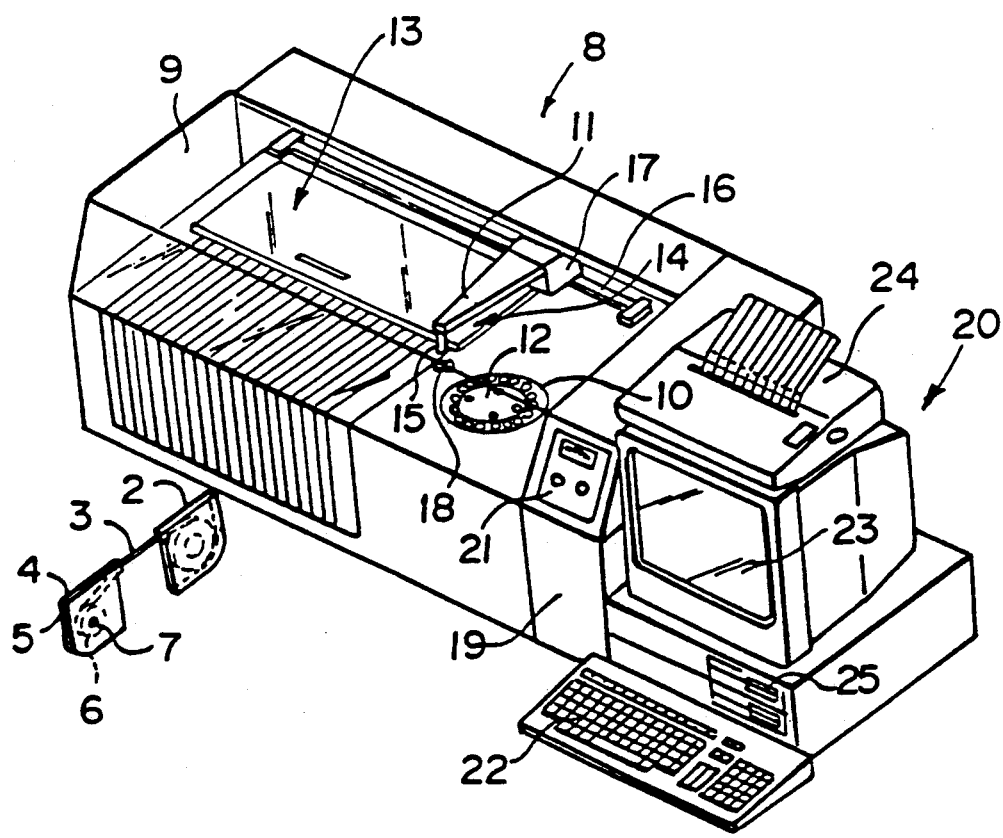
FIG. 2 is a perspective view showing an example of the biochemical analysis apparatus wherein the first long-test-film cassette for biochemical analysis in accordance with the present invention is used.

An example of the biochemical analysis apparatus wherein the long-test-film cassette 1 for biochemical analysis in accordance with the present invention is used will hereinbelow be described with reference to FIG. 2.

A biochemical analysis apparatus 8 is provided with a transparent cover 9, and a liquid sample, the long tape-like test film 3 and the like are fed into and out of the apparatus 8 by opening the cover 9. The apparatus 8 is provided with a sample accommodating means 10 for accommodating a liquid sample such as blood serum or urine along a ring-like area, and the liquid sample is taken up from the sample accommodating means 10 and applied by a sample application means 11 as will be described later. A centrifugation means 12 is provided inward from the sample accommodating means 10 for accommodating body fluid, for example, blood (whole blood), and centrifuging the blood to produce blood serum as the liquid sample, and for other purposes. The long test film 3 contains a reagent undergoing a color reaction with only a specific chemical constituent or a specific physical constituent that is to be analyzed in the liquid sample, and many kinds of the long test films 3, 3, ... are prepared in accordance with the measurement items. A test film accommodating means 13 accommodates unused portions of a plurality of the long test films 3, 3, ... in parallel so that various items of measurements can be carried out simultaneously with the apparatus 8. At the right end of the test film accommodating means 13 in FIG. 2, an electrolyte determination slide accommodating region 14 is provided for accommodating electrolyte determination slides for determination of electrolytes such as $Na^+$, $K^+$ and $Cl^-$ in the liquid sample. The unused slides are stacked in the accommodating region 14. The sample application means 11 is provided with a sample applying nozzle 15 at the end, and is moved in the extending direction of a rail 16 by a movement means 17 placed on the rail 16 for taking up the liquid sample from the sample accommodating means 10 or the centrifugation means 12, and applying the liquid sample onto the long test film 3 pulled out by a test film conveyance means from the test film accommodating means 13 or onto the electrolyte determination slide pushed out of the electrolyte determination slide accommodating region 14. The movement means 17 also moves the sample application means 11 vertically. The sample application means 11 is kept at its upper position at the time it is moved by the movement means 17 in the extending direction of the rail 16, and is moved down at the time of taking out and application of the liquid sample and at the time of washing as will be described later.

In this specification, both the electrolyte determination slide and the long test film 3 are generically referred to as the test film.

After applying the liquid sample onto the test film, the sample applying nozzle 15 is washed at a nozzle washing region 18 provided close to the electrolyte determination slide accommodating region 14 and the sample accommodating means 10 therebetween in accordance with the operation sequence as will be described later, and is reused for sample application.

The test film on which the liquid sample has already been applied is incubated by an incubator as will be described later, and subjected to measurement by a measurement means.

Control of operations of the overall apparatus 8, processing of the measurement data and the like are carried out by a circuit region 19 and a computer 20 connected therewith. An operating and display region 21 on the front surface of the circuit region 19 is provided with a power source switch for the apparatus 8, an ammeter for monitoring the current consumption in the apparatus 8, and other members. The computer 20 is provided with a keyboard 22 for giving instructions to the apparatus 8, a CRT display device 23 for displaying the subsidiary information for instructions, measurement results and other items, a printer 24 for printing the measurement results, and a floppy disk drive unit 25 for accommodating a floppy disk for storage of commands for giving various instructions to the apparatus and the information on the measurement results.

Figure 3:
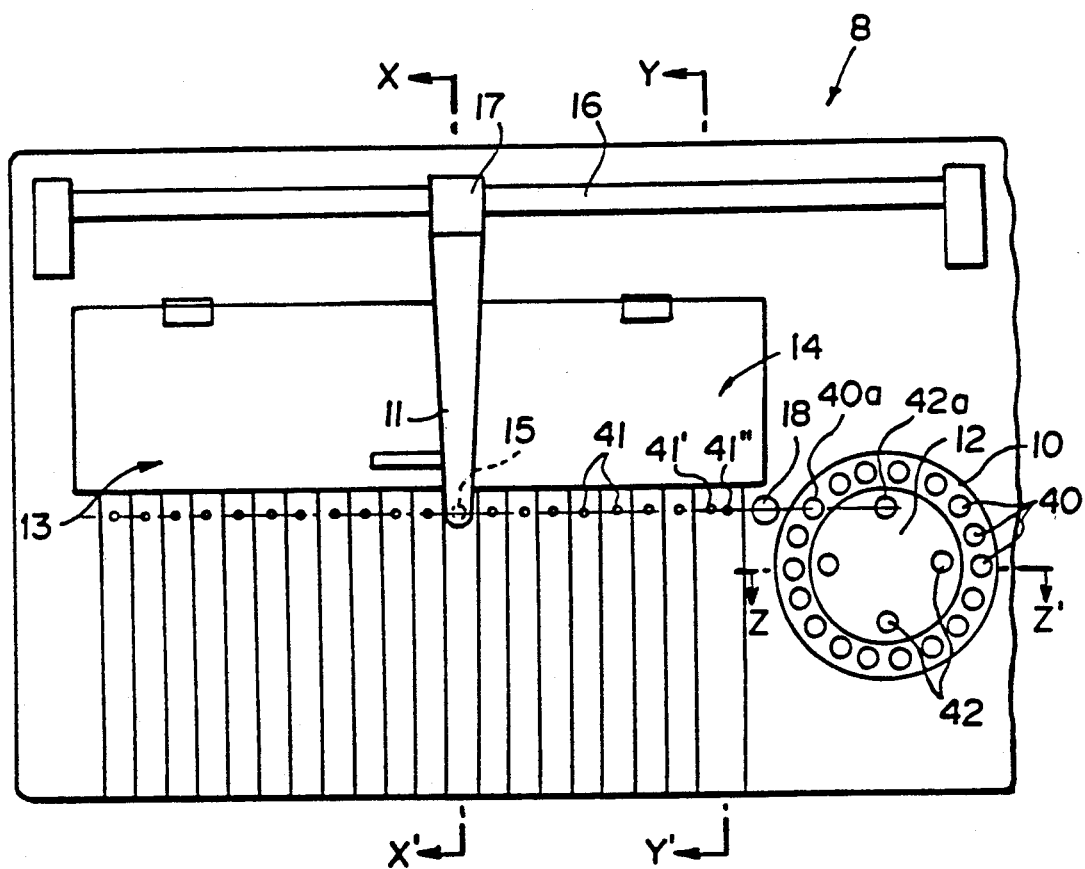
FIG. 3 is a plan view showing a major part of the biochemical analysis apparatus shown in FIG. 2.

With reference to FIG. 3 showing the major part of the apparatus 8, the test film accommodating means 13 is constituted so that sample applying positions 41, 41, ..., 41' and 41" for all of the test films pulled out or pushed out of the test film accommodating means 13 stand in a straight line indicated by the chain line. Also, the nozzle washing region 18, a liquid sample take-out position 40a in the sample accommodating means 10, and a liquid sample take-out position 42a in the centrifugation means 12 are disposed on said straight line. The arrangement on the straight line simplifies the configuration of the movement means as will be described later, which in turn contributes to a decrease in operation failures and cost of the apparatus 8.

The sample accommodating means 10 accommodates a plurality of liquid samples in accommodating regions 40, 40, ... disposed in the ring-like area. The accommodating regions 40, 40, ... are automatically rotated along the circular path until the liquid sample which is accommodated in one of the accommodating regions 40, 40, ... and which is to be used for the next measurement arrives at the take-out position 40a. In order to prevent the liquid samples accommodated in the accommodating regions 40, 40, ... from evaporating and deteriorating, a cover (not shown) is provided on the accommodating regions 40, 40, ... outside of the take-out position 40a.

The centrifugation means 12 accommodates body fluid in accommodating regions 42, 42, ..., and centrifuges it. Thereafter, as in the case of the sample accommodating means 10, the accommodating regions 42, 42, ... are rotated until the liquid sample is located at the take-out position 42a in the sequence of take-out by the sample application means 11. By way of example, the body fluid is blood (whole blood). Upon centrifugation of the whole blood, blood plasma is separated up, and blood clot sediments. In this case, blood serum or blood plasma as the liquid sample can be taken up by the sample application means 11 without being separated into a vessel different from the vessel of blood clot. As in the case of the sample accommodating means 10, a cover (not shown) is provided on the accommodating regions 42, 42, . . . of the centrifugation means 12.

The sample application means 11 is moved by the movement means 17 in the extending direction of the rail 16, takes up the liquid sample from the take-out position 40a or the take-out position 42a, and applies it to the sample applying position 41 or 41' on the test film. Both the liquid sample and a reference solution should be applied to the electrolyte determination slide, and therefore the sample applying positions 41' and 41" are provided. The liquid sample is applied to the sample applying position 41', and the reference solution is applied to the sample applying position 41".

Figure 4:
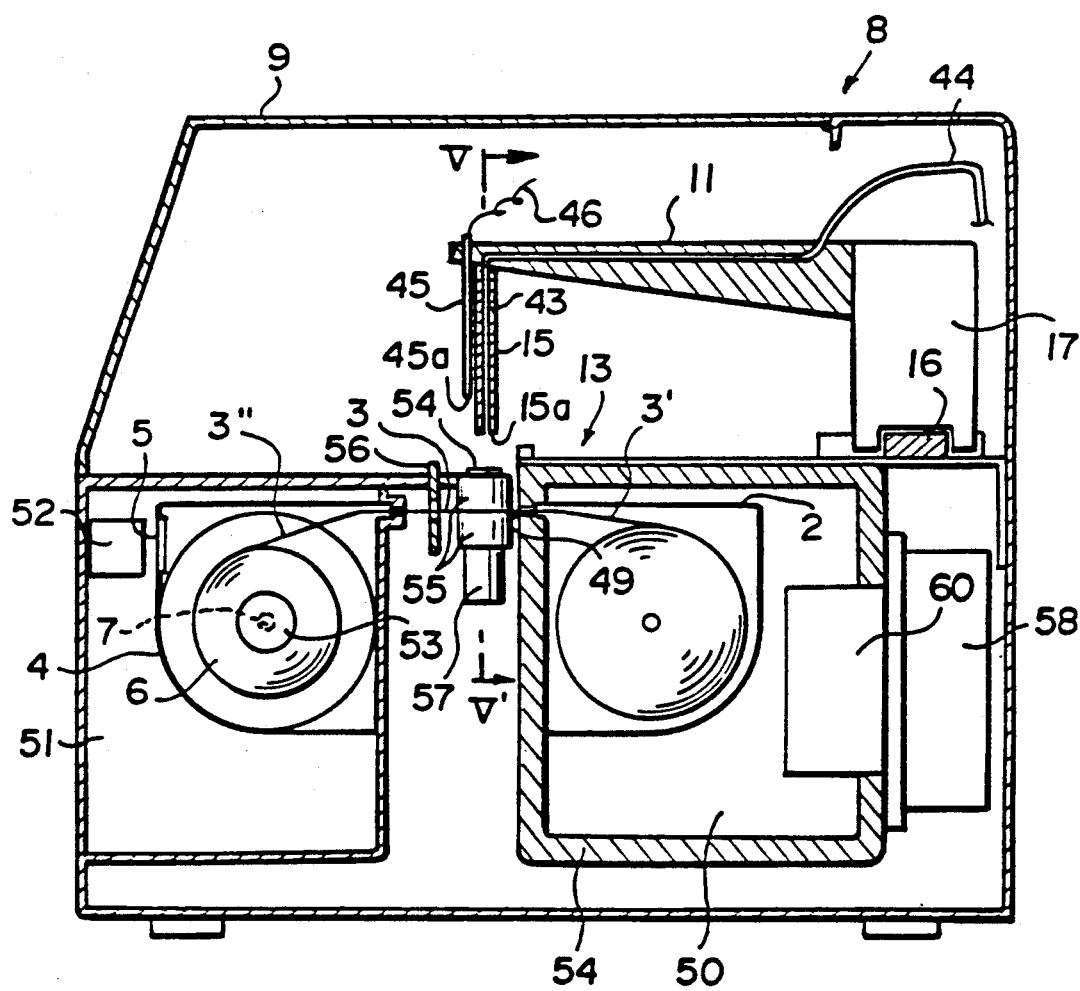
FIG. 4 is a sectional view taken along line X—X' of FIG. 3.

FIG. 4 is a sectional view taken along line X—X' of FIG. 3. In FIG. 4, similar elements are numbered with the same reference numerals with respect to FIGS. 2 and 3. With reference to FIG. 4, the long test film 3 is accommodated in the unused film cassette part 2 and the used film cassette part 4 and is accommodated in this form in the apparatus 8. The unused film cassette part 2 is accommodated in a refrigerating compartment 50 which constitutes the test film accommodating means 13, and the used film cassette part 4 is accommodated in a wind-up compartment 51.

With the configuration wherein the unused portion of the long test film 3 is accommodated in the unused film cassette part 2, the unused long test film 3 can be accommodated in the test film accommodating means 13 without the hands of the operator contacting the unused long test film 3.

As mentioned above, by way of example, the bar code 5 indicating the lot number, film number, measurement item, working life and other information on the long test film 3 is provided on one face of the used film cassette part 4. The information indicated by the bar code 5 is read by a bar code reading means 52 provided at a position in the wind-up compartment 51 corresponding to the position at which the bar code 5 is located when the used film cassette part 4 is accommodated in the wind-up compartment 51. The information thus read is stored on, for example, the floppy disk in the floppy disk drive unit 25 shown in FIG. 2, and is used for control of the measurement item and control of the length of the unused film portion remaining in the unused film cassette part 2, and elimination of measurement errors caused by fluctuations among production lots of the long test films 3, 3, . . . Also, in the case where the long test film 3 is taken out of the apparatus 8 after being used partially, the film number, the length of the remaining unused film portion and other information on the long test film 3 are stored on the floppy disk unless a deletion command is entered from the keyboard 22 shown in FIG. 2 or until the information is deleted automatically at the time the long test film 3 runs out of the working life. When the long test film 3 is again accommodated in the test film accommodating means 13 for reuse, the film number of the long test film 3 is compared with the information stored on the floppy disk, and the length of the remaining unused portion of the long test film 3 and other items are controlled again.

The aforesaid bar code 5 may be provided on the unused film cassette part 2, and the bar code reading means 52 may be provided inside of the refrigerating compartment 50. Also, the means for transmitting the lot number, the working life and other information on the long test film 3 is not limited to the bar code 5 and the means for reading the bar code 5, and any other known means for recording the information on the unused film cassette part 2 or on the used film cassette part 4 and reading the information at the time the long test film 3 is accommodated in the apparatus 8 may be employed for this purpose.

The refrigerating compartment 50 is enclosed by a refrigerating compartment wall 54 composed of a heat insulating material. A cooling and dehumidifying device 58 for keeping the inside of the refrigerating compartment 50 at a predetermined low temperature and low humidity is provided on one surface of the refrigerating compartment wall 54, and air inside of the refrigerating compartment 50 is circulated by a fan 60.

Figure 5:
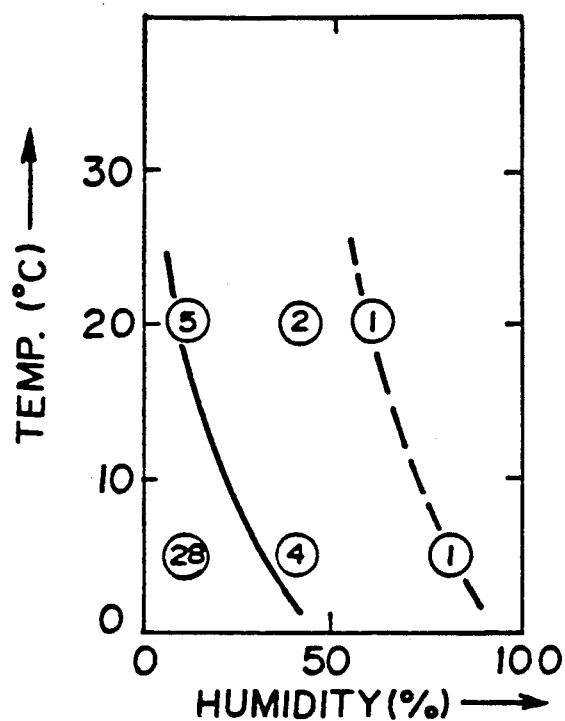
FIG. 5 is a graph showing the rates of deterioration of an unused long test film with the passage of time when the unused long test film is maintained under various temperature-humidity conditions, in terms of the number of days for which the long test film can be stored under such conditions without becoming unusable for measurement.

FIG. 5 shows the rates of deterioration of the unused long test film 3 with the passage of time when the unused long test film 3 is maintained under various temperature-humidity conditions, in terms of the number of days for which the long test film 3 can be stored under such conditions without becoming unusable for measurement. Each of the numerals indicated in the circles in FIG. 5 represents the number of days for which the long test film 3 can be stored under the temperature-humidity conditions corresponding to the circle without becoming unusable for measurement. The number of days for which the long test film 3 can be stored under the temperature-humidity conditions without becoming unusable for measurement increases sharply at the left bottom of the graph (under a low temperature, low humidity conditions) shown in FIG. 5. Therefore, the long test film 3 can be stored for a longer period in the apparatus 8 by accommodating the unused portion of the long test film 3 in the refrigerating compartment 50 and maintaining the unused portion at a predetermined low temperature and low humidity adjusted by considering the working life and the working frequency of the long test film 3 and other items.

Reverting to FIG. 4, when the used film cassette part 4 is accommodated in the wind-up compartment 51, a rotation shaft of a test film wind-up motor 53 constituting the test film conveyance means for the long test film 3 provided in the wind-up compartment 51 engages with a hole 7 formed at the center of a reel 6 of the used film cassette part 4. As the motor 53 is rotated, the long test film 3 is pulled out of the unused film cassette part 2 through a film outlet 49 of the refrigerating compartment 50, and is wound up in the used film cassette part 4. As mentioned above, the unused film cassette part 2 and the used film cassette part 4 are provided independently of each other. Therefore, the film outlet 49 of the refrigerating compartment 50 may be as small as to allow the passage of the long test film 3 therethrough, and the cooling and dehumidifying efficiency in the refrigerating compartment 50 can be maintained high. Also, the long test film 3 can also be used in various apparatuses among which the distance between the refrigerating compartment 50 and the wind-up compartment 51 differs. Furthermore, with the configuration wherein the used portion of the long test film 3 is accommodated in the used film cassette part 4, the used long test film 3 on which the liquid sample has already been applied can be taken out of the apparatus 8 and discarded without the hands of the operator contacting the used long test film 3.

The exposed portion of the long test film 3 between the unused film cassette part 2 and the used film cassette part 4 passes through an incubator 55 provided with a shutter 54 and between a light projector and a light receiver of a photoelectric switch 56. A measuring device 57 for measuring the optical density produced by a color reaction of the long test film 3 with the liquid sample is disposed under the incubator 55.

With the configuration illustrated in FIG. 4 wherein the refrigerating compartment 50 and the incubator 55 are close to each other, the length of the portion of the long test film 3 pulled out of the unused film cassette part 2 for a single measurement may be short so that more measurements can be achieved with the long test film 3 of the same length.

Figure 6:
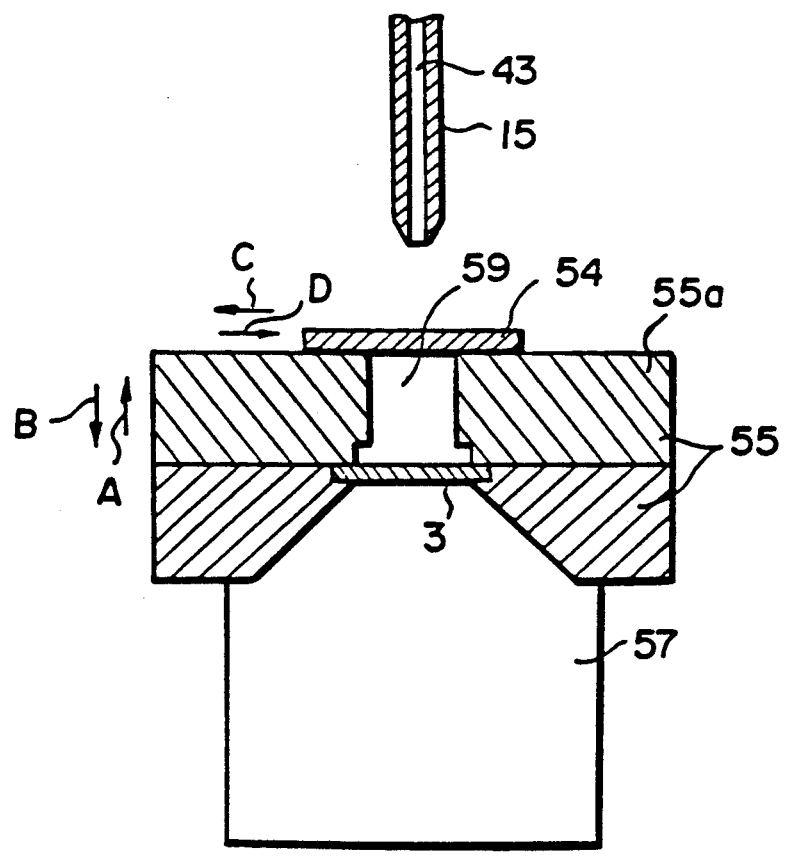
FIG. 6 is a sectional view taken along line V—V' of FIG. 4.

With reference to FIG. 6 illustrating the configuration of the incubator 55 along line V—V' of FIG. 4, the long test film 3 is pulled out of the unused film cassette part 2 and intermittently moved from the rear of the drawing sheet in FIG. 6 to the front thereof. Prior to this step, an upper cover 55a of the incubator 55 has been moved in the direction as indicated by the arrow A. After the long test film 3 has been moved as mentioned above, the upper cover 55a is moved in the direction as indicated by the arrow B, and pushes down the long test film 3 as illustrated. Then, the shutter 54 is moved in the direction as indicated by the arrow C, the sample application means 11 is moved down to apply the liquid sample from the sample applying nozzle 15 onto the long test film 3 through a hole 59. Thereafter, the shutter 54 is moved in the direction as indicated by the arrow D to close the hole 59 as illustrated and prevent air flow between the inside and outside of the hole 59, and the incubator 55 incubates so that the temperature in the inside thereof reaches a predetermined value, for example, 37° C. In the course of the incubation or after the incubation is finished, the optical density at the portion of the long test film 3 on which the liquid sample has already been applied is measured by the measuring device 57. Instead of providing the shutter 54, the upper cover 55a of the incubator 55 may be constituted moveable in the directions as indicated by the arrows C and D as well as in the directions as indicated by the arrows A and B. In this case, the upper cover 55a of the incubator 55 need not be provided with the hole 59 for sample application. But instead, after the liquid sample has been applied onto the long test film 3 by moving the upper cover 55a in the direction as indicated by the arrow C, the upper cover 55a may be moved to its original position in the direction as indicated by the arrow D, and incubation may then be carried out.

With this embodiment wherein the sample application, incubation and measurement are carried out at a single position, the position to which the liquid sample has been applied is incubated and measured reliably even though the accuracy of feed of the long test film 3 by the test film wind-up motor 53 is low. Also, since the sample applying position 41 (as shown in FIG. 3) with respect to the incubator 55 is always constant, the temperature distribution inside of the incubator 55 is constant, the color reaction is effected under constant conditions, and the measurement accuracy becomes high. Furthermore, in the case where the sample application, incubation and measurement are carried out at different positions, it is necessary for the rotation of the motor 53 to be controlled each time the long test film 3 is to be moved from the sample applying position to the incubating position or from the incubating position to the measuring position. However, with the aforesaid embodiment wherein the sample application, incubation and measurement are carried out at a single position, such complicated control is not required.

The photoelectric switch 56 shown in FIG. 4 detects holes or marks of the long test film 3. Based on the signal generated by the photoelectric switch 56, the long test film 3 is pulled out of the unused film cassette part 2 by a length necessary for a single measurement. The computer 20 shown in FIG. 2 counts the number of pull-out operations of the long test film 3, and issues a warning, for example, by sound or light, to the operator when the length of the remaining unused portion of the long test film 3 has decreased to a predetermined value or less. Also, a hole or a mark discriminable from the holes or marks provided at the predetermined length intervals on the long test film 3 by the photoelectric switch 56 is provided near the tail edge portion of the long test film 3. When the hole or mark near the tail edge portion of the long test film 3 is detected, the photoelectric switch 56 produces a signal for stopping the pull-out of the long test film 3. Alternatively, the tail edge of the long test film 3 is not secured to the unused film cassette part 2 so that the overall long test film 3 up to its tail edge is ultimately accommodated in the used film cassette part 4, and the tail edge of the long test film 3 is detected by the photoelectric switch 56. The end of the long test film 3 may be judged on the basis of only the value counted by the computer 20. However, the end mark or the like should preferably be provided on the long test film 3 itself to cope with the case wherein the long test film 3 is taken out of the apparatus 8 after it has partially been used for measurement, and is artificially wound up slightly and then loaded to the apparatus 8 again.

An elongated pipe 43 continuing into a leading end 15a of the sample applying nozzle 15 is provided in the sample application means 11. The pipe 43 is communicated with a flexible pipe 44 so that the liquid sample is fed through the pipes 43 and 44 into the sample application means 11 and applied onto the test film as will be described later. The reference solution is fed and washing liquid is delivered through the pipes 43 and 44.

A liquid level detector 45 is provided in parallel with the sample applying nozzle 15 in the vicinity thereof. The liquid level detector 45 is provided so that its leading edge 45a is slightly (for example, by approximately 2.5 mm) higher than the leading edge 15a of the sample applying nozzle 15. When the sample application means 11 is moved down by the movement means 17 for taking up the liquid sample accommodated in the sample accommodating means 10 or the centrifugation means 12, the leading edge 15a of the sample applying nozzle 15 enters the liquid sample, and the leading edge 45a of the liquid level detector 45 contacts the liquid sample. At this time, a signal indicating that the leading edge 45a of the liquid level detector 45 has contacted the liquid sample is produced by the liquid level detector 45, and transmitted to the circuit region 19 shown in FIG. 2 through a signal line 46. Based on the signal, the downward movement of the sample application means 11 is stopped. In this manner, the leading edge 15a of the sample applying nozzle 15 can be entered into the liquid sample up to a predetermined depth from the surface of the liquid sample regardless of the amount of the liquid sample.

Figure 7:
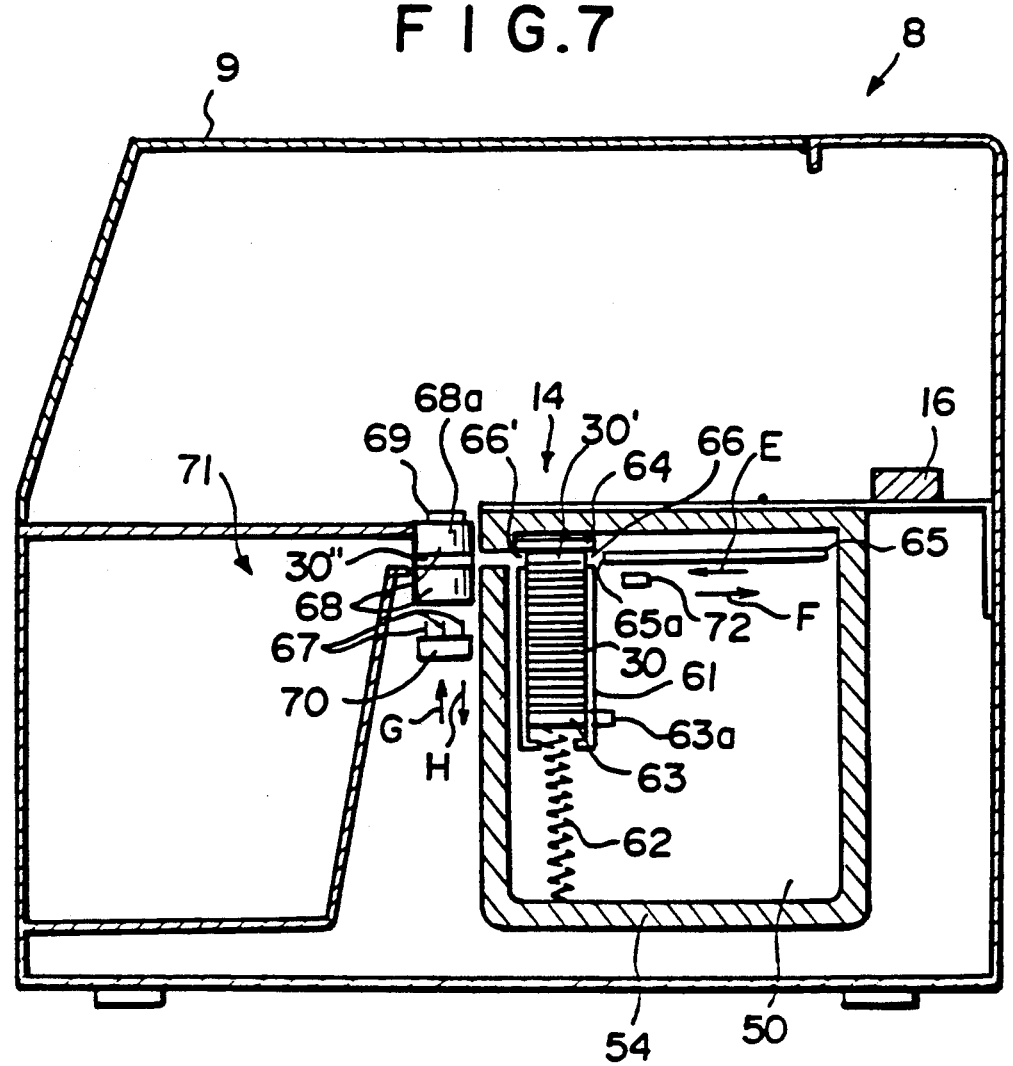
FIG. 7 is a sectional view taken along line Y—Y' of FIG. 3.

With reference to FIG. 7 illustrating the configuration of the electrolyte determination slide accommodating region 14 along line Y—Y' of FIG. 3, electrolyte determination slides 30, 30, . . . are stacked in a slide magazine 61, and a bottom plate 63 of the slide magazine 61 is urged up by a spring 62. The top slide 30' among the electrolyte determination slides 30, 30, . . . is pushed up against a top plate 64 of the slide magazine 61. A slide conveying member 65 constituting the test film conveyance means for the slides 30, 30, . . . is moveable by a drive means (not shown) in the directions as indicated by the arrows E and F. As the slide conveying member 65 is moved in the direction as indicated by the arrow E, a leading edge 65a thereof enters a slit 66 formed in the slide magazine 61, and pushes the top slide 30' in the slide magazine 61. As a result, the slide 30' is pushed out of the slide magazine 61 through a slit 66' into an incubator 68 as indicated by a reference numeral 30''. At the incubator 68, a shutter 69 is opened, a sample liquid is applied to the slide 30'', the shutter 69 is then closed, and the slide 30'' is incubated. Thereafter, a measuring device 70 is moved up in the direction as indicated by the arrow G until potential measuring probes 67, 67, 67 contact electrodes (not shown) of the slide 30'' in the incubator 68, and a difference in potential is measured. Thereafter, the measuring device 70 is moved in the direction as indicated by the arrow H to its waiting position as shown in FIG. 7. The incubator 68 has nearly the same configuration as the incubator 55 for the long test film 3 shown in FIG. 6, except that the slide 30' pushed out by the slide conveying member 65 can be accommodated as the slide 30'', and the liquid sample and the reference solution can be applied to the predetermined positions on the slide 30''. Also, instead of providing the measuring device 57 shown in FIG. 6, the probes 67, 67, 67 of the measuring device 70 moved in the direction as indicated by the arrow G in FIG. 7 contact the predetermined electrodes to measure a difference in potential.

As in the case of the long test film 3, instead of providing the shutter 69, the effect of the shutter 69 may be achieved by an upper cover 68a of the incubator 68. Also, since the sample application, incubation and measurement are carried out at a single position, the same effects as in the case of the long test film 3, such as simplification of the control of push-out of the slide 30' by the slide conveying member 65 and improved measurement accuracy, can be obtained.

After the measurement is finished, the slide 30'' is pushed by the slide conveying member 65 leftward in FIG. 7 into a slide discarding region 71. The slide conveying member 65 is then moved in the direction as indicated by the arrow F to the waiting position shown in FIG. 7.

As the slides 30, 30, . . . are pushed one by one out of the slide magazine 61, the bottom plate 63 of the slide magazine 61 is pushed up by the spring 62. At the time a protrusion 63a projecting from the bottom plate 63 out of the slide magazine 61 faces a proximity switch 72, a warning is issued to the operator to instruct replenishment of slides 30, 30, . . . In the case where a predetermined number of the slides 30, 30, . . . are then pushed out of the slide magazine without new slides replenished and the slide magazine 61 runs out of the slide 30 while the liquid sample to be measured for a difference in potential is still present, the apparatus 8 is stopped without sample application and other operations for measurement of the liquid sample being carried out.

Figure 8:
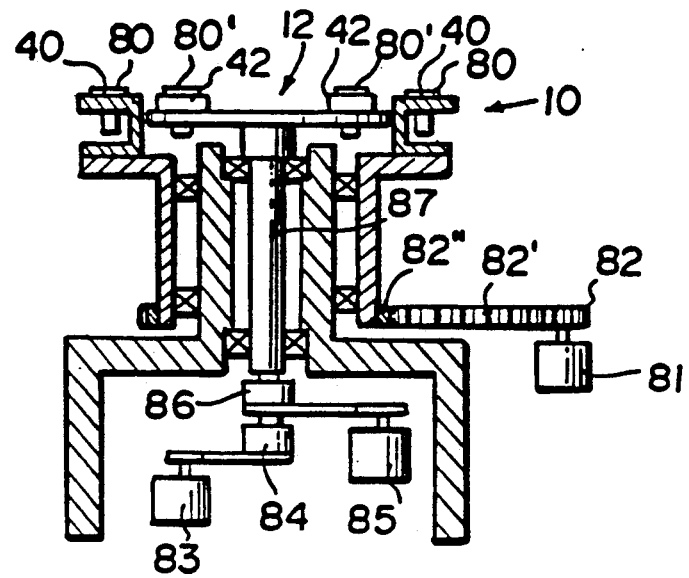
FIG. 8 is a sectional view taken along line Z—Z' of FIG. 3.

With reference to FIG. 8 illustrating the sample accommodating means 10 and the centrifugation means 12 along line Z—Z' of FIG. 3, the sample accommodating means 10 is constituted so that sample cups 80, 80, . . . for containing the liquid samples are placed in the accommodating regions 40, 40, . . . provided in the ring-like area on the upper surface of the sample accommodating means 10, and the overall sample accommodating means 10 is rotated by a motor 81 via gears 82, 82' and 82''. The operation of the motor 81 is controlled so that the liquid samples are located one after another at the liquid sample take-out position 40a shown in FIG. 3 in the sequence of take-out from the sample accommodating means 10 and sample application.

Sample cups 80', 80', . . . containing body fluid are placed in the accommodating regions 42, 42, . . . on the upper surface of the centrifugation means 12. From the viewpoint of cup control and reduction in cost, cups of the same type as the sample cups 80, 80, . . . on the sample accommodating means 10 are employed as the sample cup 80', 80', . . .

A motor 83 is provided for centrifugation. A motor 85 rotates the sample cups 80', 80', . . . to locate the liquid sample (body fluid) after centrifugation at the liquid sample take-out position 42a shown in FIG. 3 as in the case of the motor 81.

At the time centrifugation is to be carried out, a clutch 86 is disengaged to disconnect the motor 85 from a rotation shaft 87, and a clutch is engaged to transmit the power of the motor 83 to the rotation shaft 87. The motor is operated in this condition to rotate the sample cups 80', 80', . . . at a high speed with the bottoms of the sample cups 80', 80', . . . facing outward and openings thereof facing inward by the centrifugal force so that the body fluid does not spill out of the sample cups 80', 80', . . . After centrifugation is thus carried out for a predetermined time, the clutch 84 is disengaged to disconnect the motor 83 from the rotation shaft 87, and the clutch 86 is engaged to connect the motor 85 to the rotation shaft 87. The motor 85 is then operated to rotate the sample cups 80', 80', . . . until the liquid sample (body fluid) after centrifugation is located at the liquid sample take-out position 42a.

As the centrifugation means 12 is provided in the space inward from the sample accommodating means 10, the overall apparatus 8 can be made small. Also, since the accommodating regions 42, 42, . . . of the centrifugation means 12 are provided inward from the accommodating regions 40, 40, . . . arranged in the ring-like area of the sample accommodating means 10, feed of the liquid sample (body fluid) to the apparatus 8 for measurement can be carried out at a single position, and therefore a high operating efficiency can be obtained.

Figure 9:
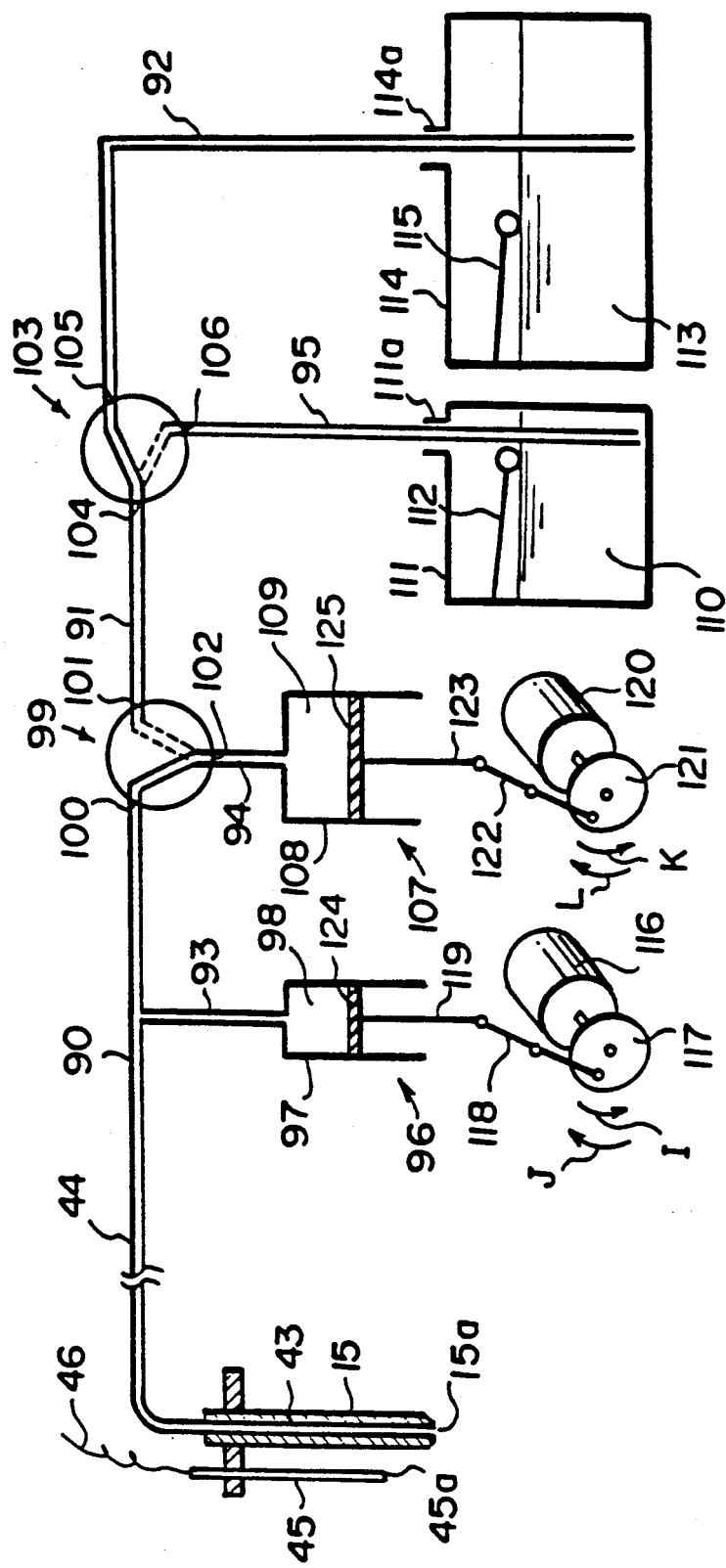
FIG. 9 is a flow diagram showing the pipes communicating with a pipe of a sample application nozzle.

With reference to FIG. 9 showing the pipes communicating with the pipe 43 passing through the center of the sample applying nozzle 15 of the sample application means 11, the pipe 43 communicates with the flexible pipe 44 which communicates with an end of a pipe 90. The pipe 90 communicates at its intermediate point with a pipe 93 communicating with a space 98 in a cylinder 97 of a suction and delivery means 96, and the other end of the pipe 90 is connected to a port 100 of a solenoid valve 99. A pipe 91 connects a port 101 of the solenoid valve 99 with a port 104 of a solenoid valve 103. A port 102 of the solenoid valve 99 is connected to a pipe 94 communicating with a space 109 in a cylinder 108 of a suction and delivery means 107. The solenoid valve 99 is changed over by a signal received from the exterior to communicate the pipes 90 and 94 with each other and disconnect the pipe 91 from the pipe 94, or conversely to communicate the pipes 91 and 94 with each other and disconnect the pipe 90 from the pipe 94. A port 106 of the solenoid valve 103 is connected to an end of a pipe 95 having the other end extending to the vicinity of the bottom of a tank 111 via an opening 111a of the tank 111 and immersed in a reference solution 110 in the tank 111. A liquid level detector 112 is provided in the tank 111 for detecting the level of the reference solution 110 in the tank 111. A signal indicating the level of the reference solution 110 is transmitted to the circuit region 19 shown in FIG. 2 via a signal line (not shown), and a warning is issued by, for example, sound or light, to the operator when the level of the reference solution 110 is low. A port 105 of the solenoid valve 103 is connected to an end of a pipe 92 having the other end extending to the vicinity of the bottom of a tank 114 via an opening 114a of the tank 114 and immersed in a washing liquid 113 in the tank 114. As in the case of the tank 111, a liquid level detector 115 is provided in the tank 114. The solenoid valve 103 is changed over by a signal received from the exterior to communicate the pipes 91 and 92 with each other and disconnect the pipe 91 from the pipe 95, or conversely to communicate the pipes 91 and 95 with each other and disconnect the pipe 91 from the pipe 92.

The suction and delivery means 96 sucks the liquid sample from the leading edge 15a of the sample applying nozzle 15, and applies it therefrom onto the test film. In order to sucks the liquid sample, the leading edge 15a of the sample applying nozzle 15 is entered into the liquid sample accommodated in the sample accommodating means 10 or the centrifugation means 12 until the leading edge 45a of the liquid level detector 45 contacts the surface of the liquid sample, and the solenoid valve 99 is controlled so that the pipes 90 and 94 disconnect from each other and the pipes 91 and 94 communicate with each other. In this condition, the motor 116 is rotated in the direction as indicated by the arrow I, the rotation force is converted into linear motion via a cam plate 117 and a link mechanism 118, and the linear motion is transmitted to a piston rod 119. As a result, the piston rod 119 is moved down to pull a piston 124 down and broaden a space 98 inside of the cylinder 97. In this manner, the liquid sample is moved from the leading edge 15a of the sample applying nozzle 15 to the pipes 43, 44 and 90. In order to apply the liquid sample onto the test film, the sample application means 11 is moved to the sample applying position of the test film, the shutter 54 or the shutter 69 is opened, the sample applying nozzle 15 is moved down, and then the motor 116 is rotated in the direction as indicated by the arrow J. As a result, the drive force of the motor 116 is transmitted to the piston rod 119 via the cam plate 117 and the link mechanism 118, the piston rod 119 is moved up to push the piston 124 up, and the liquid sample is applied in an amount corresponding to the extent of the movement of the piston 124.

In order to deliver the reference solution 110 from the leading edge 15a of the sample applying nozzle 15, the solenoid valve 99 is first controlled so that the pipes 91 and 94 communicate with each other and the pipes 90 and 94 are disconnected from each other, and the solenoid valve 103 is controlled so that the pipes 91 and 95 communicate with each other and the pipes 91 and 92 are disconnected from each other. In this condition, the motor 120 is rotated in the direction as indicated by the arrow K, the rotation force is converted into linear motion via a cam plate 121 and a link mechanism 122, and the linear motion is transmitted to a piston rod 123. As a result, the piston rod 123 is moved down to pull a piston 125 down and broaden a space 109 inside of the cylinder 108. In this manner, the reference solution 110 is moved through the pipe 95, the solenoid valve 103, the pipe 91, the solenoid valve 99 and the pipe 94 into the space 109 in the cylinder 108. Then, the solenoid valve 99 is controlled so that the pipes 90 and 94 communicate with each other and the pipes 91 and 94 are disconnected from each other. Thereafter, the motor 120 is rotated in the direction as indicated by the arrow L to move the piston rod 123 up and push the piston 125 up, and the reference solution 110 is delivered from the leading edge 15a of the sample applying nozzle 15 in an amount corresponding to the extent of movement of the piston 125.

Delivery of the washing liquid 113 from the leading edge 15a of the sample applying nozzle 15 is controlled in the same manner as the delivery of the reference solution 110, except that the solenoid valve 103 is controlled so that the pipes 91 and 92 communicate with each other and the pipes 91 and 95 are disconnected from each other when the washing liquid 113 is to be moved to the space 109 in the cylinder 108.

With the aforesaid pipe connections, the sample applying nozzle 15 works for both the liquid sample and the reference solution, and it is not necessary to use dual nozzles as disclosed in, for example, Japanese Unexamined Patent Publication No. 61(1986)-173131. With this embodiment wherein a single nozzle is used, the mechanism is simplified, operation failures decrease, and the cost decreases.

Also, with the aforesaid embodiment wherein the opening 111a of the tank 111 containing the reference solution 110 is made as small as to allow insertion of the pipe 95 thereinto, evaporation and deterioration of the reference solution 110 can be prevented as compared with the case where the reference solution 110 is kept to stand in the sample cups 80, 80, ... at the accommodating regions 40, 40, ... as in the case of the liquid sample. Furthermore, with the substantially large tank 111, no replenishment of the reference solution 110 thereto is required for a long period.

Operations of the biochemical analysis apparatus shown in FIG. 2 will be described hereinbelow. It is ordinarily practiced that a monitor means for monitoring the operating condition is provided on the apparatus 8, thereby automatically carrying out processing such as stop of the apparatus 8 and issuance of a warning to the operator in the case of abnormal operation. Therefore, processing in the case of abnormal operation will be only briefly described below.

First, the power source switch of the apparatus 8 is turned on by the operator to supply electric power to the apparatus 8 only after the necessary test film has been accommodated in the apparatus 8. In the case where the power switch is off and the test film is present in the test film accommodating means 13, the cooling and dehumidifying device 58 is kept energized to maintain the inside of the refrigerating compartment 50 at a predetermined temperature and humidity.

After the electric power is supplied to the apparatus 8, initial setting of the apparatus 8 is carried out in the sequence described below. Specifically, in the case where the sample application means 11 is not at its upper position, it is moved to its upper position by the movement means 17. The sample application means 11 is then moved by the movement means 17 to a predetermined end of the rail 16.

Thereafter, the sample application means 11 is moved by the movement means 17 toward the washing region 18, and is stopped by a signal received from a position detection means (not shown) for producing the signal at the time the sample application means 11 arrives at the washing region 18. On the other hand, by way of example, a pulse encoder (not shown) is provided on a shaft of a motor (not shown) for moving the sample application means 11 along the rail 16. The pulses produced by the pulse encoder in proportion to the amount of rotation of the motor are counted during the movement of the sample application means 11 from the predetermined end of the rail 16 to the washing region 18. Based on the number of the pulses counted, the presence or absence of slipping between the shaft of the motor and the movement of the sample application means 11 along the rail 16 is detected.

The positions of the pistons 124 and 125 shown in FIG. 9 are monitored to detect whether they are or are not at their start positions that make the space 98 and the space 109 smallest. In the case where the pistons 124 and 125 are not at their start positions, the motors 116 and 120 are rotated in the directions as indicated by the arrows J and L, respectively, to move the pistons 124 and 125 to their start positions. At this time, the solenoid valve 99 is controlled so that the pipes 90 and 94 communicate with each other. In the case where there has been liquid remaining in, for example, the space 109 in the cylinder 108, the liquid is delivered from the leading edge 15a of the sample applying nozzle 15 to the washing region 18 via the pipe 43.

The shutter 54 shown in FIG. 4 and the shutter 69 shown in FIG. 7 are monitored to detect whether they are present at the positions closing the incubators 55 and 68, and the inside of the incubator 55 and the inside of the incubator 68 are maintained at the predetermined temperature.

Also, monitor is effected to detect whether, for example, the levels of the reference solution 110 and the washing liquid 113 in the tanks 111 and 114 are or are not higher than the predetermined levels, and whether the measuring device 70 and the slide conveyance means 65 are or are not at their waiting positions. Then, issuance of a warning to the operator when necessary and automatic shifting to the initial condition are carried out.

After the apparatus 8 has been set to the initial condition in the manner described above, the completion of the initial setting is indicated to the operator.

Thereafter, the operator pours the liquid sample which need not be centrifuged into the sample cup 80 and places it at a predetermined position in the sample accommodating means 10. Body fluid requiring centrifugation is poured into the sample cup 80', and the sample cup 80' is placed at a predetermined position in the centrifugation means 12. The information on the measuring item for the liquid sample (body fluid) is entered from the keyboard 22 or from a floppy disk storing the information inserted into the floppy disk drive unit 25. The apparatus 8 automatically detects whether the test film corresponding to the measuring item thus specified has been or has not been accommodated in the test film accommodating means 13. Also, the position of the liquid sample (body fluid) in the sample accommodating means 10 (centrifugation means 12) is entered to the apparatus 8 from, for example, the keyboard 22. In the case where measurement is to be carried out for a plurality of the liquid samples (body fluids), the aforesaid operations are repeated.

Thereafter, a measurement start instruction is given by the operator to the apparatus 8 by use of, for example, the keyboard 22, and the automatic measuring operations are started.

First, in the case where the body fluid samples have been accommodated at the centrifugation means 12, centrifugation is carried out by the operations of the motors 83, 85 and the clutches 84, 86. After the centrifugation, the body liquid samples (liquid samples) are located one after another at the liquid sample take-out position 42a in the sequence of measurement.

In the case where the liquid samples have been accommodated at the sample accommodating means 10, they are located one after another at the liquid sample take-out position 40a in the sequence of measurement.

Thereafter, the sample application means 11 positioned at the washing region 18 in the initial condition is moved to suck the liquid sample from the sample accommodating means 10 or the centrifugation means 12 into the pipes 43, 44 and 90 by broadening the space 98 in the cylinder 97 while the level of the liquid sample is monitored by means of the liquid level detector 45. In the case where a plurality of measurements are to be carried out, in order to complete suction of the liquid sample by a single operation and shorten the overall measurement time, the liquid sample is sucked in an amount sufficient for all measurements. At this time, the pipes 43, 44 and 90 have often been filled with the washing liquid by the washing operation as will be described later. Therefore, before the liquid sample is thus sucked, air is slightly sucked into the pipe 43 with the leading edge 15a of the sample applying nozzle 15 present in air, and the leading edge 15a of the sample applying nozzle 15 is then entered into the liquid sample. As a result, an air layer intervenes between the washing liquid and the sucked liquid sample so that they do not mix together.

Then, the sample application means 11 is moved up and moved along the rail 16 to the sample applying position on the test film specified in advance. The case where the liquid sample is applied onto the long test film 3 and the case where it is applied onto the slide 30 will hereinbelow be described separately.

First, in the case where the liquid sample is to be applied to the long test film 3, sample application to the long test film 3 is first carried out even though sample application to the slide 30 is necessary, thereby to shorten the overall measurement time. As described above with reference to FIG. 6, sample application to the long test film 3 is carried out by the operations of the shutter 54 and the upper cover 55a of the incubator 55. In order to minimize deterioration of the long test film 3 with the passage of time, the long test film 3 is pulled out of the unused film cassette part 2 by the test film conveyance means exactly prior to the sample application.

In the case where the liquid sample is to be applied to a plurality of the long test films 3, 3, . . . , in order to minimize the movement of the sample application means 11 and shorten the overall measurement time, the sample application is basically carried out sequentially from the long test film 3 accommodated at an end among the long test films 3, 3, ... toward the one at the other end. However, in the case where the measurement sequence is specified by the operator when, for example, measurement results of a measurement item are to be investigated urgently, the sample application is carried out in the specified sequence.

After the liquid sample has been applied to the long test film 3, the long test film 3 is incubated, and the optical density at the portion applied with the liquid sample is measured. The measurement results are fed to the computer 20, necessary calculation processing is carried out, and the results of calculation processing are stored and fed out.

Sample application to the slide 30 is carried out as described below.

In the case where sample application is to be carried out for both the slide 30 and the long test film 3, sample application to the long test film 3 is first carried out in the manner as mentioned above, and then the sample application means 11 is moved to the sample applying position 41' of the slide 30, and the liquid sample is applied to the slide 30 in the manner as mentioned above. As in the case of the long test film 3, in order to prevent deterioration of the slide 30, conveyance of the slide 30 from the refrigerating compartment 50 to the predetermined position by the slide conveyance member 65 is carried out exactly prior to the sample application to the slide 30. After the liquid sample has been applied to the slide 30, the sample application means 11 is moved to the nozzle washing region 18. A small vessel (not shown) is placed at the nozzle washing region 18. By way of example, distilled water is contained in the vessel and is made to run so that fresh distilled water is always contained in the vessel. After being moved to the nozzle washing region 18, the sample application means 11 is moved down by the movement means 17 until the leading edge 15a of the sample applying nozzle 15 enters the distilled water.

During the movement of the sample application means 11, the reference solution 110 is accumulated in the cylinder 108 show in FIG. 9 by the above-mentioned operations. After the leading edge 15a of the sample applying nozzle 15 has been entered to the distilled water, the liquid sample remaining in the pipe 43 and other pipes is delivered from the leading edge 15a of the sample applying nozzle 15. In the case where the pipe 90 and other pipes have been filled with the washing liquid, the washing liquid is then delivered. Also, the reference solution 110 which has slightly been mixed with the washing liquid in the pipe 90 and other pipes is delivered. As a result, the reference solution 110 is filled in the pipes up to the leading edge 15a of the sample applying nozzle 15.

The reference solution 110 is then applied to the predetermined on the slide 30. The reference solution 110 should be applied to the slide 30 as early as possible (for example, within 3 seconds) after the liquid sample has been applied to the slide 30, and therefore the application of the liquid sample to the slide 30 is carried out after the sample application to the necessary long test film 3 has been finished. With this procedure, when sample application is necessary for both the long test film 3 and the slide 30, take-out of the liquid sample from the sample accommodating means 10 or the centrifugation means 12 can be completed by a single operation, and the overall measurement time can be shortened. The measurement time for the slide 30 ($Na^+$, $K^+$, $Cl^-$ potential difference measurement item) is approximately one minute, whereas the measurement time for the long test film 3 (color reaction) is approximately four minutes on the average. Therefore, in order to shorten the overall measurement time, measurement for the slide 30 should be carried out last. Also, since the sample applying positions 41' and 41'' for the slide 30, the nozzle washing region 18, and the sample accommodating means 10 are provided close to one another, the distance of movement of the sample application means 11 between the step of application of the liquid sample to the slide 30 and the step of application of the reference solution to the slide 30 by the aforesaid operations can be minimized, and the overall measurement time can further be shortened.

The slide 30 on which the liquid sample and the reference solution have already been applied is incubated in the manner as mentioned above, and the difference in potential is measured. The measurement results are fed to the computer 20, necessary calculation processing is carried out, and the results of calculation processing are stored and fed out.

After the sample application is finished in the manner as mentioned above, the sample application means 11 is moved to the nozzle washing region 18, and the leading edge 15a of the sample applying nozzle 15 is immersed in distilled water. Thereafter, the pistons 124 and 125 are moved to their start positions if they were not there, and the liquid sample, the reference solution and the like are delivered from the leading edge 15a of the sample applying nozzle 15. The washing liquid is then accumulated in the cylinder 108 by the above-mentioned operations, and delivered from the leading edge 15a of the sample applying nozzle 15 for the purpose of washing.

In the case where the liquid sample which is to be determined next is still present in the sample accommodating means 10 or the centrifugation means 12 after the aforesaid operations have been finished, the liquid sample is moved to the liquid sample take-out position 40a or 42a, and the aforesaid operations are repeated.

Another embodiment of the first long-test-film cassette for biochemical analysis in accordance with the present invention will hereinbelow be described with reference to FIGS. 10 to 18.

Figure 10:
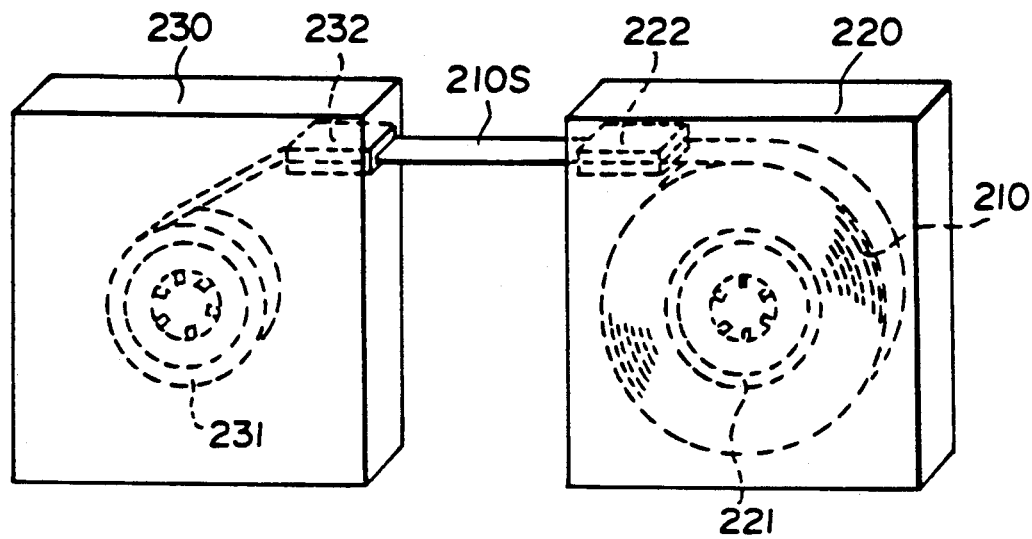
FIG. 10 is a perspective view showing another embodiment of the first long-test-film cassette for biochemical analysis in accordance with the present invention with an unused film cassette part and a used film cassette part spaced away from each other.

FIG. 10 shows another embodiment of the first long-test-film cassette for biochemical analysis in accordance with the present invention with an unused film cassette part and a used film cassette part spaced away from each other.

With reference to FIG. 10, a long test film 210 is accommodated in an unused film cassette part 220 in a roll form wound around a reel 221. The leading edge portion of the long test film 210 is pulled out of the unused film cassette part 220 via its film outlet portion 222, introduced into a used film cassette part 230 provided independently of the unused film cassette part 220 via a film inlet portion 232 of the used film cassette part 230, and secured to a reel 231 in the used film cassette part 230. Application of the liquid sample, incubation and measurement are carried out at a film portion 210S of the long test film 210 exposed between the unused film cassette part 220 and the used film cassette part 230.

Figure 11A:
FIGS. 11A, 11B and 11C are perspective views showing examples of the long test film usable in the long-test-film cassette for biochemical analysis in accordance with the present invention.

By way of example, as shown in FIG. 11A, the long test film 210 is a colorimetric analysis test film having multi-layer analysis elements. With reference to FIG. 11A, the colorimetric analysis test film 210 comprises a light-permeable support 211, a reagent layer 212 overlaid on the support 211, and a spreading layer 213 overlaid on the reagent layer 212. In biochemical analysis, the liquid sample is applied onto the spreading layer 213, and is allowed to spread therethrough. An analysis objective constituent of the liquid sample migrates to the reagent layer 212, and reacts with the reagent contained in the reagent layer 212. A change in color density produced by the color reaction of the analysis objective constituent with the reagent is measured by irradiating light from the side of the support 211 and measuring the light reflected by the colorimetric analysis test film 210, thereby to analyze the analysis objective constituent contained in the liquid sample based on the principle of colorimetry. The colorimetric analysis test film 210 may also be provided with other layers known in the art such as a reflection layer, a light-shielding layer, a filter layer, a registration layer, a water absorbing layer and a prime coat layer. Also, the spreading layer 213 and the reagent layer 212 may be constituted by a single layer.

The configuration of the multi-layer analysis element shown in FIG. 11A is already known.

By way of example, the support 211 is constituted by a film of a light-permeable, water-impervious material, for example, a polymer such as polyethylene terephthalate, bisphenol-A polycarbonate, polystyrene, or a cellulose ester (e.g. cellulose diacetate, cellulose triacetate, or cellulose acetate propionate). The thickness of the support 11 should preferably be within the range of approximately 50 $\mu$m to approximately 300 $\mu$m, more preferably within the range of 80 $\mu$m to 200 $\mu$m. The width of the support 11 should preferably be within the range of approximately 3 mm to 10 mm. The length of the support 11 may be selected in accordance with the number of analyses per roll, which is not limited particularly. In general, it is advantageous that the length of the support 11 be equivalent to 100 to 600 analysis regions.

The spreading layer 213 horizontally spreads the liquid sample applied to the surface thereof approximately at a predetermined rate per unit area substantially without maldistribution of the constituent contained in the liquid sample. The spreading layer 213 is formed of a paper such as a filter paper, or a knitted, woven or non-woven fabric of a natural fiber or a synthetic fiber. Also, the spreading layer 213 may be constituted by a porous material of a particulate polymer.

In order to control spreading of the liquid sample, the spreading layer 213 may also contain a hydrophilic polymer such as a cellulose derivative, polyvinyl pyrrolidone, polyvinyl alcohol or polyacrylamide, a surface active agent such as a nonionic surface active agent, a cationic surface active agent, an anionic surface active agent or an amphoteric surface active agent, and/or a buffer suitable for achieving analysis reliably.

The reagent layer 212 contains a reagent suitable for producing a change in color density detectable with colorimetry upon reaction with the analysis objective constituent. The reagent layer 212 should preferably be prepared by dispersing at least one kind of reagent in a hydrophilic colloid (as a binder) of, for example, gelatin, a gelatin derivative, polyvinyl alcohol, polyacrylamide, or polyvinyl pyrrolidone.

Figure 11B:
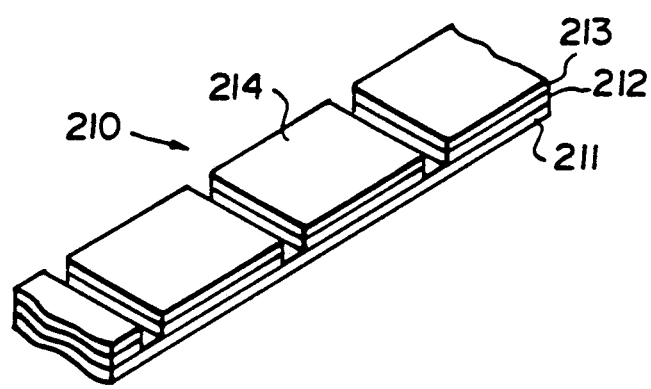
Figure 11C:
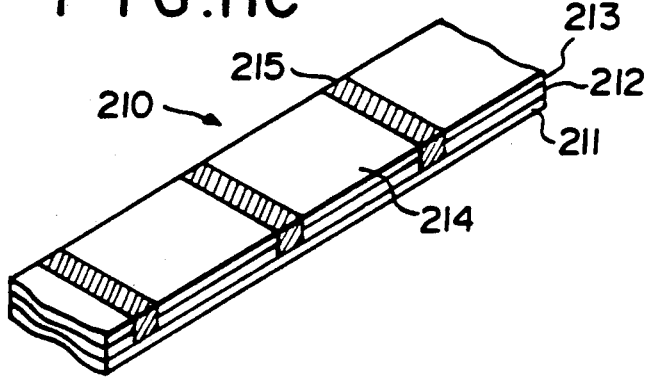

The multi-layer analysis element may be of any configuration insofar as the support 211 is a long film. For example, as shown in FIG. 11A, the region outside of the support 211, e.g. the reagent layer 212 and/or the spreading layer 213, may be formed long as is the support 211. Alternatively, as shown in FIG. 11B, the reagent layer 212 and the spreading layer 213 may be divided in the unit of a single analysis region 214. Or, as shown in FIG. 11C, in the case where the reagent layer 212 and the spreading layer 213 are continuous, a barrier portion 215 for obstructing migration of the liquid sample may be provided at the boundary between adjacent analysis regions 214, 214.

Another example of the long test film 210 is a test film provided with sheet-like ion selective electrodes for measuring the ionic activity of a liquid sample by applying the liquid sample and a reference solution respectively to ion selective layers of the ion selective electrodes, which ion selective layers are electrically isolated from each other, and measuring a difference in potential between the ion selective electrodes.

Reverting to FIG. 10, the unused film cassette part 220 and the used film cassette part 230 have nearly the same size capable of accommodating therein the overall length of the long test film 210 by winding it around the reel 221 or the reel 231. The cross-sectional shapes of the unused film cassette part 220 and the used film cassette part 230 need not necessarily be square as shown in FIG. 10, and may be rectangular, circular and any other shape. However, they should preferably be square or rectangular for easy processing of the cassette parts 220 and 230 during loading to the analysis apparatus. The unused film cassette part 220 and the used film cassette part 230 can be fabricated by a known method. For example, the case and the cover of each cassette part may be made independently, and secured to each other by fitting, engagement, fixing with screws, adhesion and any other means after the unused long test film has been accommodated in the case. Alternatively, the case and the cover may be coupled by a hinge on one side of the cover.

When the long test film 210 is wound up in a too small curvature radius, it will crack. Therefore, the diameters of the reels 221 and 231 should not be so small. In general, their diameters should preferably be within the range of 40 mm to 80 mm. Also, engagement members for wind-up and stop of the long test film 210 are provided inside of the reels.

In general, the unused film cassette part 220, the used film cassette part 230 and the reels 221, 231 can be easily made from various thermoplastic resins, for example, polyolefin resins such as polyethylene and polypropylene, styrene resins such as polystyrene, high-impact polystyrene, a styrene-acrylonitrile resin and an ABS resin, a polyvinyl chloride resin, nylon, polyester, polycarbonate, polyacetal and other resins by utilizing the technique ordinarily used for making audio or video cassette tapes.

The long-test-film cassette for biochemical analysis described above with reference to FIG. 10 is constituted so that the unused film cassette part 220 and the used film cassette part 230 are joined readily releasably. An embodiment of such a long-test-film cassette for biochemical analysis will hereinbelow be described with reference to FIG. 12.

Figure 12:
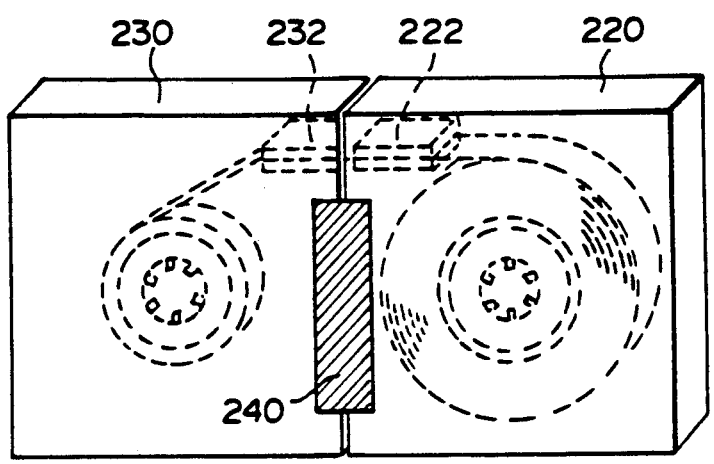
FIG. 12 is a schematic view showing a further embodiment of the first long-test-film cassette for biochemical analysis in accordance with the present invention.

With reference to FIG. 12, the unused film cassette part 220 and the used film cassette part 230 are put close to each other so that the film outlet portion 222 and the film inlet portion 232 stand facing each other, and an adhesive tape 240 is adhered across the unused film cassette part 220 and the used film cassette part 230 to join them together. The adhesive tape 240 may be applied to a part of the unused film cassette part 220 and the used film cassette part 230, or over the overall circumference of the boundary therebetween. When the long-test-film cassette is to be used for measurement, the adhesive tape 240 is peeled off, and the unused film cassette part 220 and the used film cassette part 230 thus released from each other are loaded to predetermined positions in the analysis apparatus.

Figure 13:
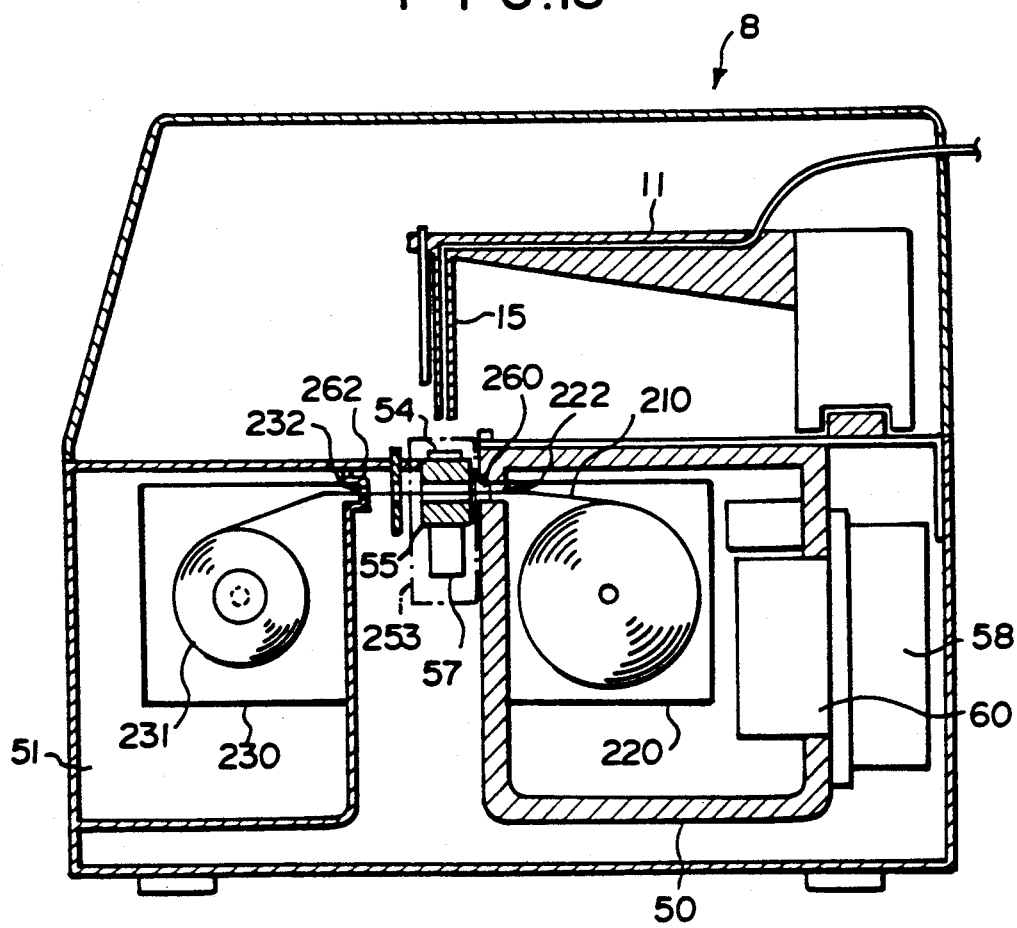
FIG. 13 is a sectional view showing an example of the colorimetric analysis apparatus wherein the embodiment shown in FIG. 10

FIG. 13 shows an example of a colorimetric analysis apparatus 8 wherein the long-test-film cassette for colorimetric analysis shown in FIG. 10 is used. In FIG. 13, similar elements are numbered with the same reference numerals with respect to FIG. 4. With reference to FIG. 13, the sample application means 11 is provided at the upper part of the colorimetric analysis apparatus 8, and the sample applying nozzle 15 connected with the sample application means 11 is provided exactly above an analysis region 253 at the central region of the colorimetric analysis apparatus 8. The shutter 54, the incubator 55 and the measuring device 57 are provided in the analysis region 253. The refrigerating compartment 50 is provided at the lower part of the colorimetric analysis apparatus 8, and is maintained at a predetermined low temperature and low humidity by the cooling and dehumidifying device 58 and the fan 60.

The unused film cassette part 220 is fitted in the refrigerating compartment 50 so that the film outlet portion 222 is positioned in a film outlet hold 260 of the refrigerating compartment 50 and the reel is rotatable. The used film cassette part 230 is fitted in the wind-up compartment 51 so that the film inlet portion 232 is positioned in a film inlet hole 262 of the wind-up compartment 51 and the reel 231 is rotatable by a drive shaft (not shown) of the colorimetric analysis apparatus 8. The long test film 210 passes through the film outlet hole 260 of the refrigerating compartment 50, the inside of the incubator 55, and the film inlet hole 262 of the wind-up compartment 51.

In order to analyze the liquid sample by the colorimetric analysis apparatus 8 shown in FIG. 13, the long test film 210 is pulled out of the unused film cassette part 220 and moved to the analysis region 253, and the liquid sample is applied from the sample applying nozzle 15 to an analysis region of the long test film 210. The incubator 55 is then closed by the shutter 54, and the analysis region of the long test film 210 is incubated at a predetermined temperature (for example, 37° C.) for a predetermined time in the incubator 55. Midway during or after the incubation, the optical density of the analysis region of the long test film 210 is measured by the measuring device 57. Based on the measured optical density, the analysis objective constituent in the liquid sample can be analyzed quantitatively.

Instead of using the adhesive tape 240 shown in FIG. 12, releasable joining of the unused film cassette part 220 and the used film cassette part 230 to each other may be achieved in various other manners, for example, as shown in FIGS. 14A to 18.

Figure 14A:
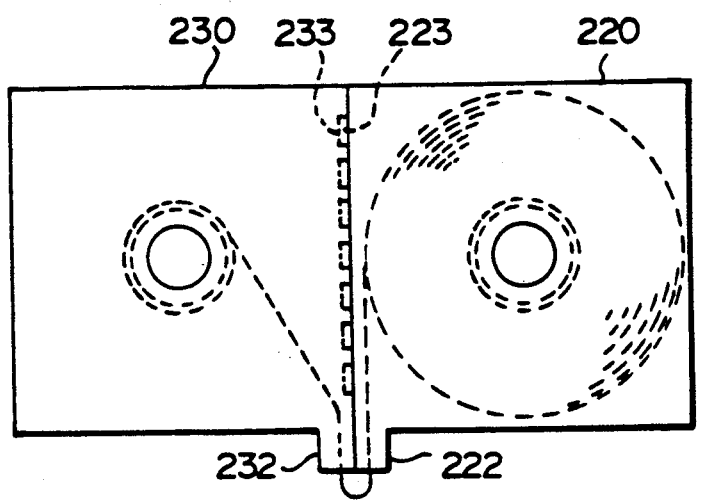
Figure 14B:
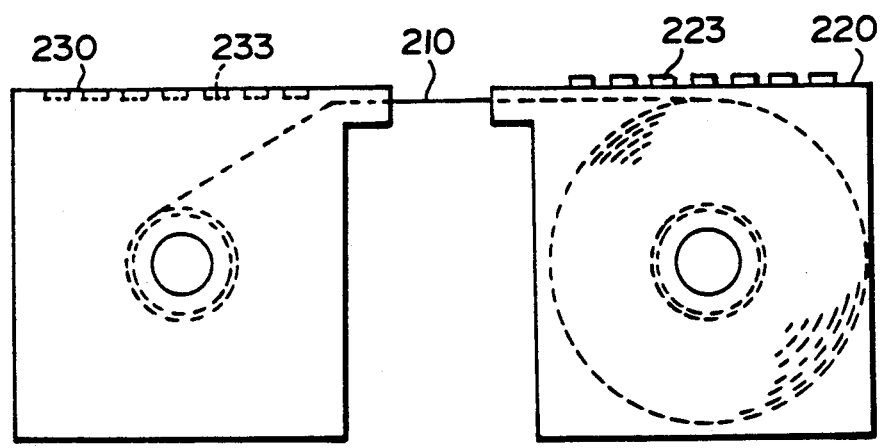

With reference to FIG. 14A, the unused film cassette part 220 and the used film cassette part 230 are put close to each other so that the film outlet portion 222 and the film inlet portion 232 face the same direction adjacent to each other. Small protrusions 223 are provided on the surface of the unused film cassette part 220 facing the used film cassette part 230, and recesses 233 of nearly the same shapes as the protrusions 223 are provided on the used film cassette part 230 at positions corresponding to the protrusions 223. The protrusions 223 are fitted into the recesses 233, thereby to releasably join the unused film cassette part 220 and the used film cassette part 230 together. Instead of the point-like protrusions 223 and the recesses 233, a linear protrusion and a linear recess may be provided. Also, conversely to the aforesaid configuration, the protrusion or protrusions may be provided on the used film cassette part 230, and the recess or recesses may be provided on the unused film cassette part 220. In the case where the unused film cassette part 220 and the used film cassette part 230 are formed of a thermoplastic resin as mentioned above, the readily releasable joining of the unused film cassette part 220 and the used film cassette part 230 to each other can be achieved easily by utilizing the known molding technique. In order to load the long-test-film cassette shown in FIG. 14A to the analysis apparatus, the unused film cassette part 220 and the used film cassette part 230 are slightly bent at an angle nearly normal to the drawing sheet in FIG. 14A and released from each other. Then, they are loaded to the analysis apparatus as shown in FIG. 14B. In the case where the linear protrusion and the linear recess are provided, the unused film cassette part 220 and the used film cassette part 230 are slid up and down in FIG. 14A and thus released from each other.

Figure 15A:
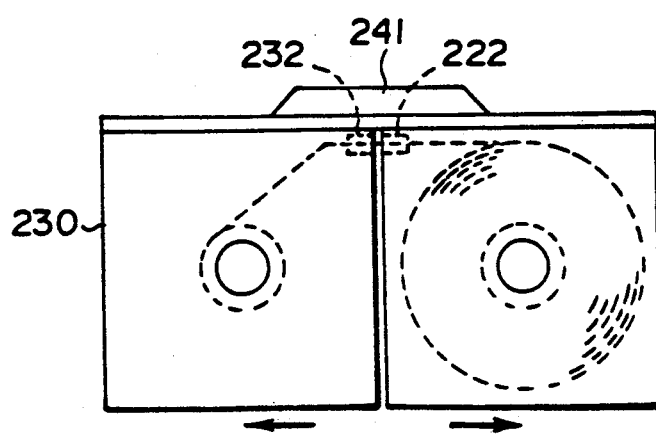
Figure 15B:
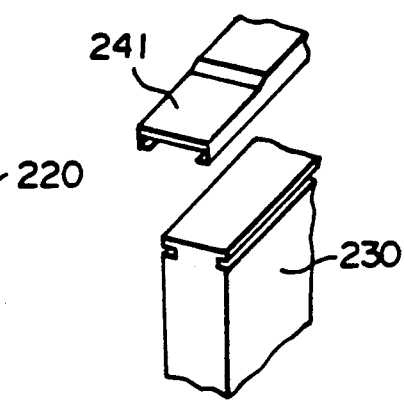

With reference to FIG. 15, the unused film cassette part 220 and the used film cassette part 230 are put close to each other so that the film outlet portion 222 and the film inlet portion 232 stand facing each other, and the upper surfaces of the unused film cassette part 220 and the used film cassette part 230 are fitted slideably to an engagement member 241. The cassette parts 220 and 230 may instead be engaged with the engagement member 241 by means of a combination of point-like protrusions (or a linear protrusion) with poin-like recesses (or a linear recess) as mentioned above with reference to FIG. 14A. FIG. 15A shows an example of the engagement of the cassette parts 220 and 230 with the engagement member 241. In this case, in order to load the cassette parts 220 and 230 to the analysis apparatus, they may be moved horizontally and disengaged from the engagement means 241.

Figure 16:
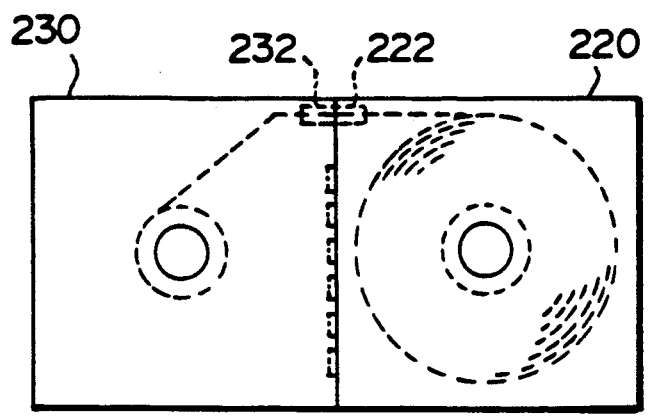

With reference to FIG. 16, the unused film cassette part 220 and the used film cassette part 230 are put close to each other so that the film outlet portion 222 and the film inlet portion 232 stand facing each other, and the side surfaces of the unused film cassette part 220 and the used film cassette part 230 are slideably fitted to each other. The cassette parts 220 and 230 may instead be engaged with each other by means of a combination of point-like protrusions (or a linear protrusion) with point-like recesses (or a linear recess) as mentioned above with reference to FIG. 14A. In order to release the cassette parts 220 and 230 from each other, they may be moved vertically in FIG. 16 with respect to each other or bent with respect to each other.

Figure 17:
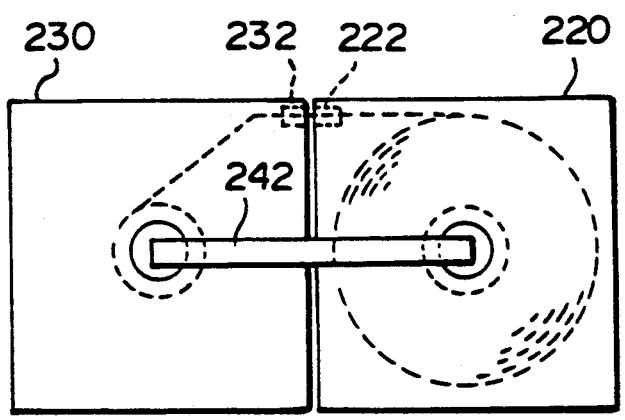

With reference to FIG. 17, the unused film cassette part 220 and the used film cassette part 230 are put close to each other so that the film outlet portion 222 and the film inlet portion 232 stand facing each other, and edge portions of an engagement member 242 are fitted into the drive holes of the reels 221 and 231. The cassette parts 220 and 230 can be released from each other simply by removing the engagement member 242.

Figure 18:
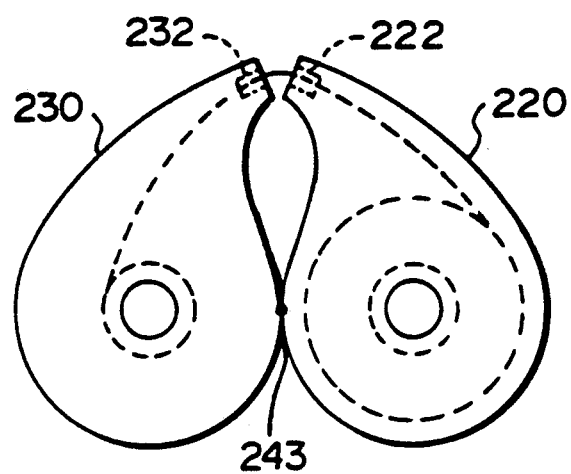

With reference to FIG. 18, the unused film cassette part 220 and the used film cassette part 230 of generally circular shapes having the film outlet portion 222 and the film inlet portion 232 slightly protruded are joined together by a small area, for example, a small point-like, string-like or thin film-like area, at a point of contact 243 between the cassette parts 220 and 230. The cassette parts 220 and 230 can easily be formed with the conventional technique so that they are readily releasable at the point of contact 243.

With the embodiments of the long-test-film cassette for biochemical analysis shown in FIGS. 10 to 18 wherein the unused film cassette part 220 and the used film cassette part 230 are provided independently of each other and joined releasably, the cassette can be processed very easily between the production step and the loading to the analysis apparatus. Also, when the cassette is to be used for analysis, the cassette parts 220 and 230 can be readily separated from each other and loaded to the analysis apparatus independently.

Cassette packs as further embodiments of the first long-test-film cassette for biochemical analysis in accordance with the present invention will hereinbelow be described with reference to FIGS. 19A, 19B, 20A and 20B. In FIGS. 19A, 19B, 20A and 20B, similar elements are numbered with the same reference numerals with respect to FIG. 10. In the long-test-film cassette packs for biochemical analysis, the unused film cassette part 220 and the used film cassette part 230 are packed in a single container so that the long test film 210 do not twist nor move so much. The packing form is not limited to a particular one.

Figure 19A:
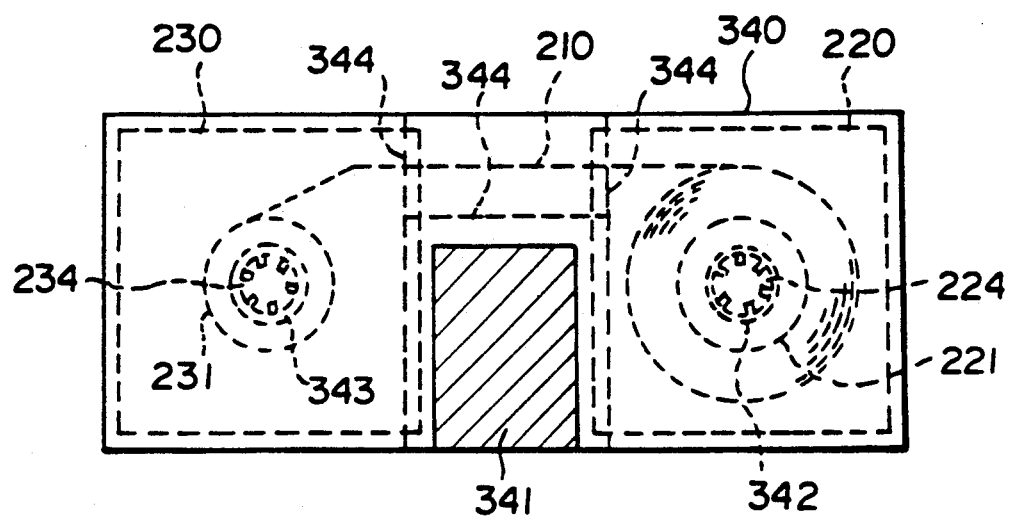
FIGS. 19A and 19B are a front view and a perspective view showing a still further embodiment of the first long-test-film cassette for biochemical analysis in accordance with the present invention.
Figure 19B:
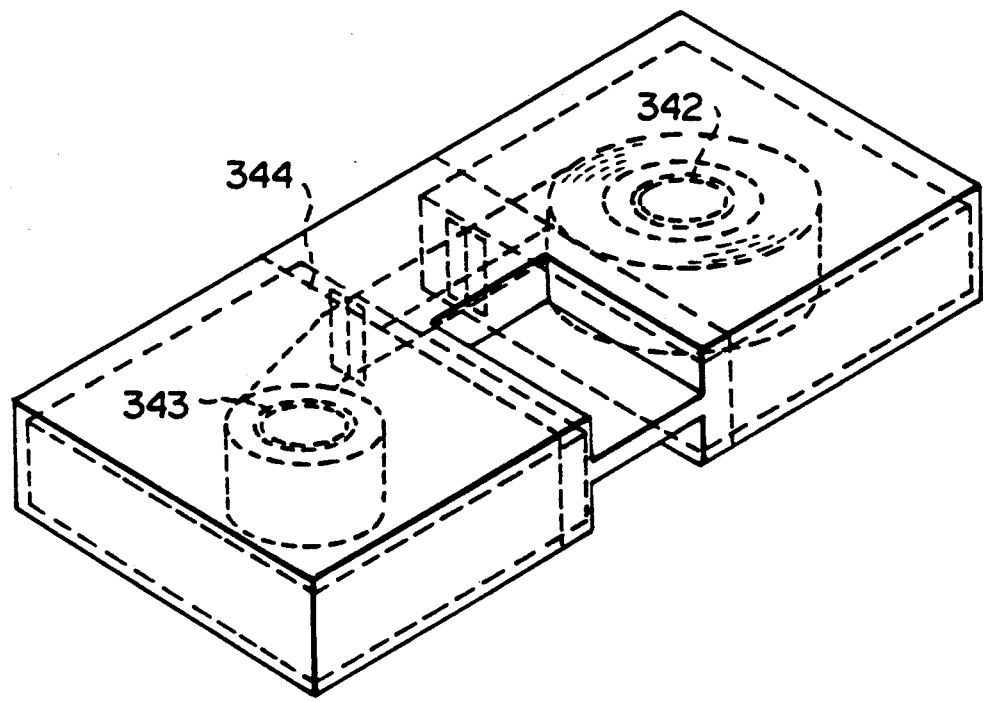

With reference to FIGS. 19A and 19B, the unused film cassette part 220 accommodating the long test film 210 and the used film cassette part 230 in which the leading edge portion of the long test film 210 is secured to the reel 231 are spaced away from each other by a distance equal to the analysis region of the long test film 210 and housed in this condition in a bag-like container 340. The front and rear surfaces of the container 340 are joined to each other at a joining area 341 between the unused film cassette part 220 and the used film cassette part 230 so that the cassette parts 220 and 230 do not move so much in the container 340. The container 340 is provided with perforations 342 and perforations 343 at the positions respectively corresponding to a shaft receiving hole 224 of the unused film cassette part 220 and a shaft receiving hole 234 of the used film cassette part 230. The cassette parts 220 and 230 can be fitted to drive shafts or supporting shafts of the analysis apparatus by breaking the container 340 along the perforations 342 and the perforations 343. The container 340 is also provided with perforations 344. When the long-test-film cassette is to be loaded to the analysis apparatus, the container 340 is broken along the perforations 344 to expose the necessary portion of the long-test-film cassette without the unused film cassette part 220 and the used film cassette part 230 taken out of the container 340. During storage prior to the use of the long-test-film cassette, the perforations 342, 343 and 344 should preferably be covered by tapes or the like for preventing the long test film 210 from being deteriorated by ambient air. As the distance between the shaft receiving holes 224 and 234 is matched to the corresponding dimension in the analysis apparatus, the film cassette can be loaded quickly to the analysis apparatus. Instead of loading the film cassette in the packed form to the analysis apparatus, the unused film cassette part 220 and the used film cassette part 230 may be taken out of the container 340 and loaded to the analysis apparatus. The perforations 342, 343 and 344 may be of any type insofar as the container 340 can be broken readily. Also, the perforations 342, 343 and 344 may be omitted, or the perforations 344 may be provided at any other position. The joining area 341 may be of any other shape insofar as the unused film cassette part 220 and the used film cassette part 230 do not move so much. However, the joining area 341 should preferably have a large area as shown in FIG. 19A in order to prevent deformation of the pack during its processing and to prevent deformation of the long test film 210 between the unused film cassette part 220 and the used film cassette part 230 as much as possible.

The container 340 may be made of a material such as a paper, a film or a sheet or a molding of a thermoplastic resin as mentioned above, or a combination thereof. A known method may be employed for making the container 340 by use of such a material.

Figure 20A:
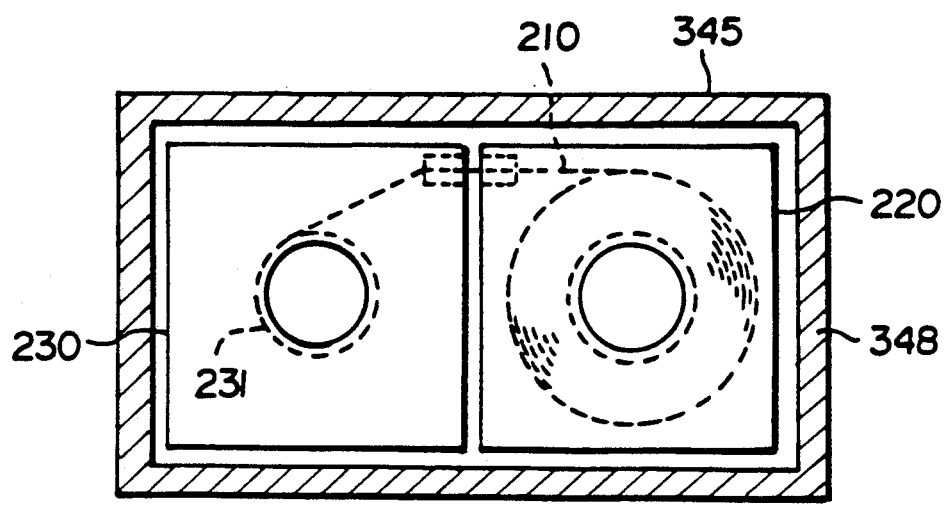
FIGS. 20A and 20B are a front view and an exploded perspective view showing an even still further embodiment of the first long-test-film cassette for biochemical analysis in accordance with the present invention.
Figure 20B:
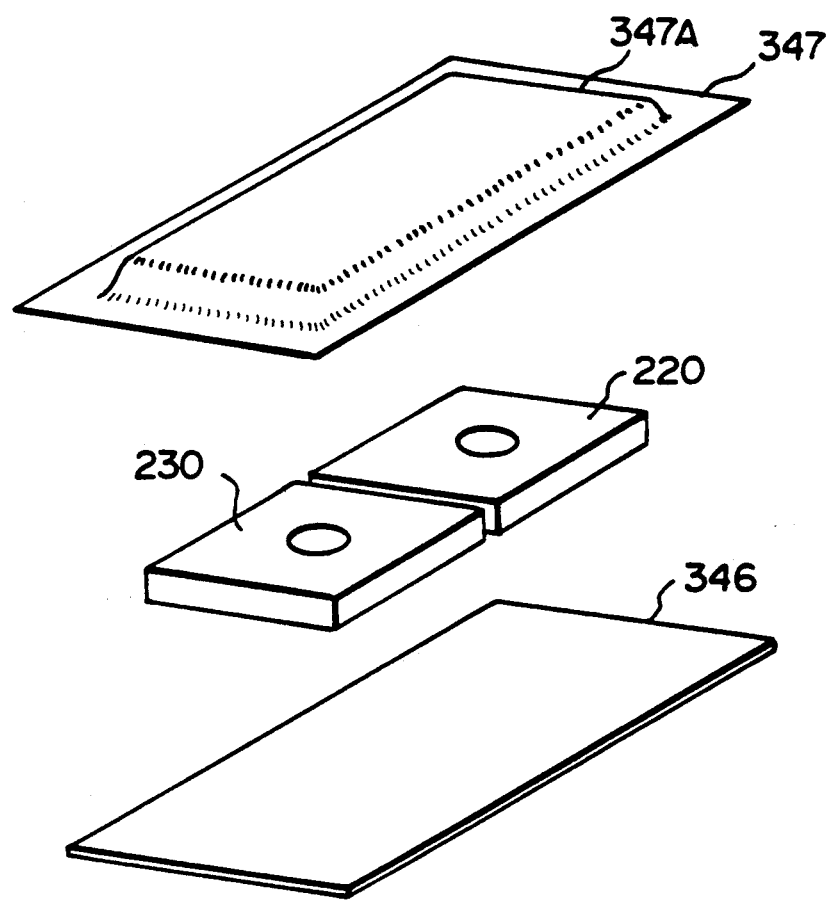

With reference to FIGS. 20A and 20B showing another example of the cassette pack, the unused film cassette part 220 accommodating the long test film 210 and the used film cassette part 230 in which the leading edge portion of the long test film 210 is secured to the reel 231 are housed close to each other in a container 345.

The container 345 is constituted by joining a bottom member 346 and a cover member 347 by adhesion or fusion at the peripheral portions thereof. The cover member 347 is provided with a cover recess 347A slightly larger than the unused film cassette part 220 and the used film cassette part 230 so that the cassette parts 220 and 230 do not move so much in the container 345.

In order to prevent deformation of the cassette pack and facilitate discrimination of the cassette, the bottom member 346 should preferably be made of a thick, rigid material and the cover member 347 should preferably be made of a thin, transparent material. Also, the bottom member 346 and the cover member 347 may be coupled by a hinge only at one side.

Instead of the configuration shown in FIG. 20A, the unused film cassette part 220 and the used film cassette part 230 may be spaced from each other, and the bottom member 346 or the cover member 347 may be provided with recesses for receiving the unused film cassette part 220, the used film cassette part 230 and the long test film 210 therebetween.

The container 345 may be made of a material such as a paper, a film or a sheet or a molding of a thermoplastic resin as mentioned above, or a combination thereof. A known method may be employed for making the container 345 by use of such a material.

With the embodiments shown in FIGS. 19A, 19B, 20A and 20B wherein the unused film cassette part 220 and the used film cassette part 230 are packed in a single container, the cassette parts 220 and 230 can be processed as a single pack prior to the use, and can be loaded to the analysis apparatus without being taken out of the packing container. Thus the film cassette can be processed easily. Also, the cassette parts 220 and 230 can readily be taken out of the packing container and loaded independently of each other to the analysis apparatus when necessary, and therefore the film cassette can be used in various types of analysis apparatuses having different processing capacity. Furthermore, in the case where the packing container is constituted to completely seal the film cassette therein, the long test film 210 can be stored shielded from ambient air up to the use step and prevented from deterioration.

Embodiments of the second long-test-film cassette for biochemical analysis in accordance with the present invention will hereinbelow be described with reference to FIGS. 21 to 26.

Figure 21:
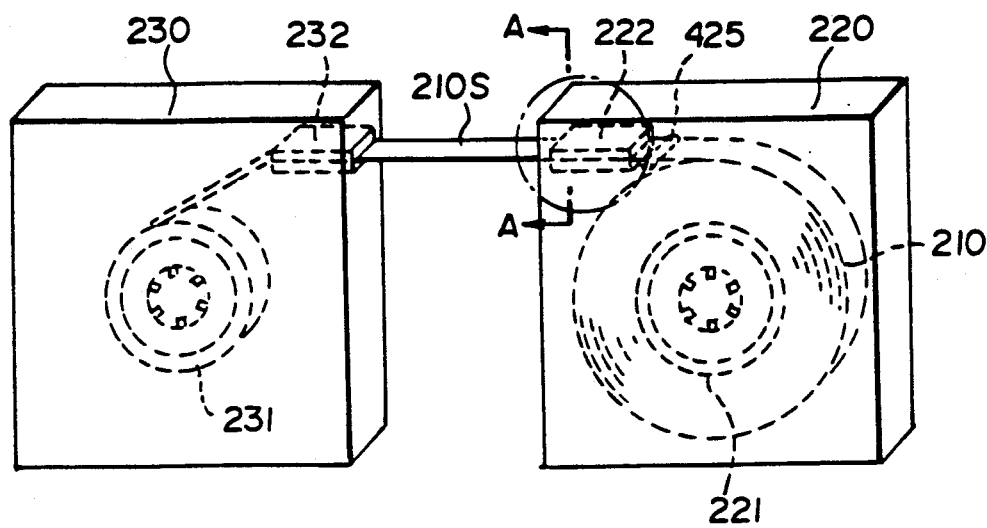
FIG. 21 is a perspective view showing an embodiment of the second long-test-film cassette for biochemical analysis in accordance with the present invention with an unused film cassette part and a used film cassette part spaced away from each other.

FIG. 21 is a perspective view showing an embodiment of the second long-test-film cassette for biochemical analysis in accordance with the present invention. In FIG. 21, similar elements are numbered with the same reference numerals with respect to FIG. 10. The configuration of the film outlet portion 222 of the unused film cassette part 220 in this embodiment will hereinbelow be described in detail.

Figure 22:
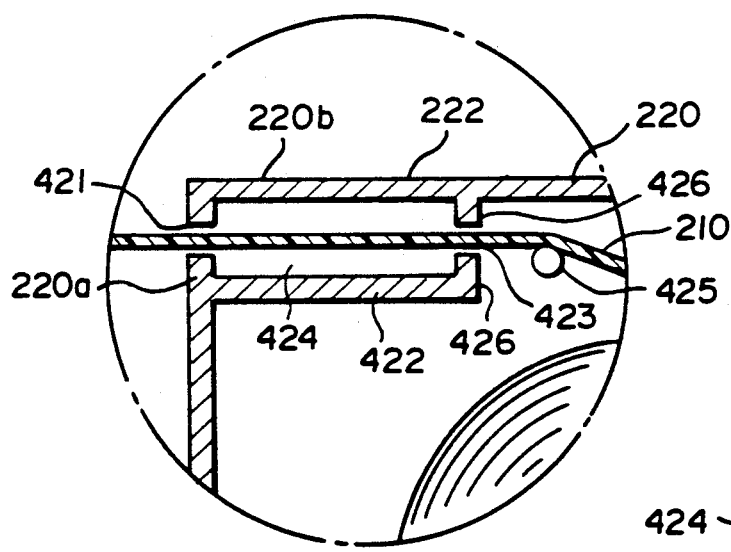
FIGS. 22, 23, 24, 25 and 26 are enlarged sectional views showing examples of the configurations of the film outlet portion of the unused film cassette part in the embodiment shown in FIG. 21.
Figure 23:
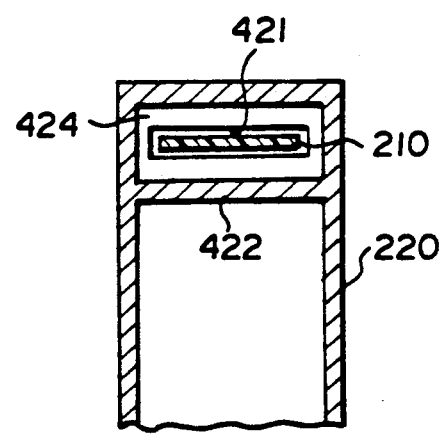

FIG. 22 is an enlarged sectional view showing the portion indicated in the circle in FIG. 21, and FIG. 23 is a sectional view taken along line A—A of FIG. 21. With reference to FIGS. 22 and 23, a film outlet hole 421 is formed in a side wall 220a of the unused film cassette part 220, and a plate member 422 is provided in the unused film cassette part 220 to stand facing an upper wall 220b of the unused film cassette part 220 with the long test film 210, which passes through the film outlet hole 421, intervening therebetween, so that an elongated channel 424 is formed by the plate member 422 and the upper wall 220b. A blocking member 426 having a film passage hole 423 of a size allowing the passage of the long test film 210 therethrough is provided on the side of the channel 424 opposite to the film outlet hole 421. The film outlet portion 222 having the channel configuration is constituted in this manner. A guide roller 425 for guiding the long test film 210 and making smooth the movement of the long test film 210 to the film outlet portion 222 is provided close to the film outlet portion 222. The height of the channel 424 should preferably be made small to such an extent that the movement of the long test film 210 therethrough is not obstructed, and the length of the channel 424 should preferably be made long within a range allowable in the unused film cassette part 220 accommodating the long test film 210. The blocking member 426 need not necessarily be provided, depending on the shape of the channel 424. Instead of forming the channel 424 by the upper wall 220b of the unused film cassette part 220 and the plate member 422 as shown in FIG. 22, the channel 424 may be formed by two plate members. The plate member 422 and the blocking member 426 may be formed integrally with the unused film cassette part 220 during the manufacture of the unused film cassette part 220, or may be produced independently of the unused film cassette part 220 and incorporated thereinto or secured thereto.

Figure 24:
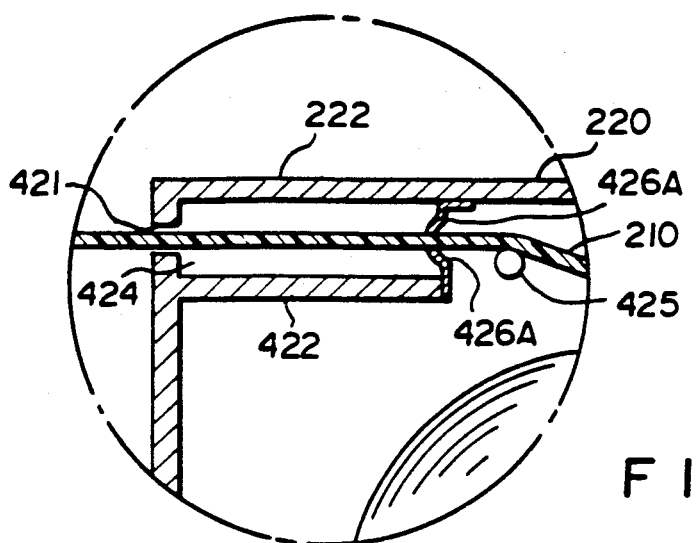

FIG. 24 shows the film outlet portion of the unused film cassette part in another embodiment of the second long-test-film cassette for biochemical analysis in accordance with the present invention. This embodiment is the same as the embodiment shown in FIG. 22, except that a resilient member 426A is provided instead of the blocking member 426 shown in FIG. 22. The resilient member 426A is slightly tilted inwardly toward the channel 424, and the leading edge of the resilient member 426A slightly contacts the long test film 210. The resilient member 426A should preferably be formed of a film or a sheet of rubber, a thermoplastic resin or the like. A plurality of resilient members 426A, 426A, . . . may be provided in the channel 424.

Figure 25:
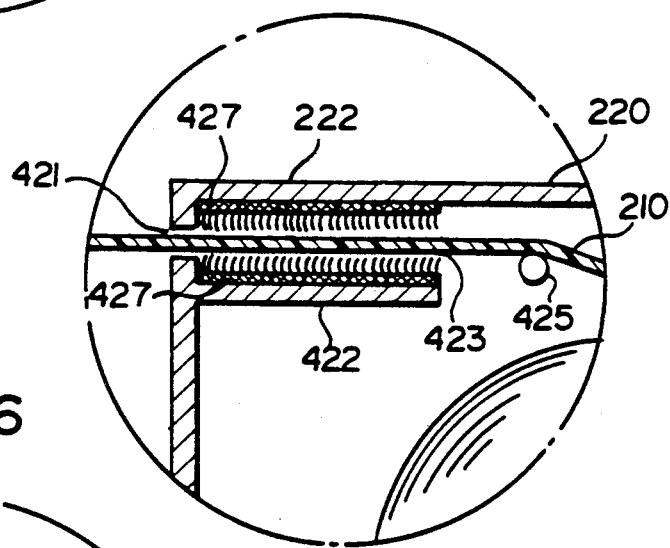

FIG. 25 shows the film outlet portion of the unused film cassette part in a further embodiment of the second long-test-film cassette for biochemical analysis in accordance with the present invention. In this embodiment, piled materials 427, 427 are provided to sandwich the long test film 210 in the channel 424 shown in FIG. 22. In this embodiment, the blocking member 426 need not necessarily be provided. The piled materials 427, 427 may be selected from, for example, velvet, mat, velveteen, a cloth electrostatically flocked with fibers or yarns, and other known materials. Felt may also be employed for this purpose.

Figure 26:
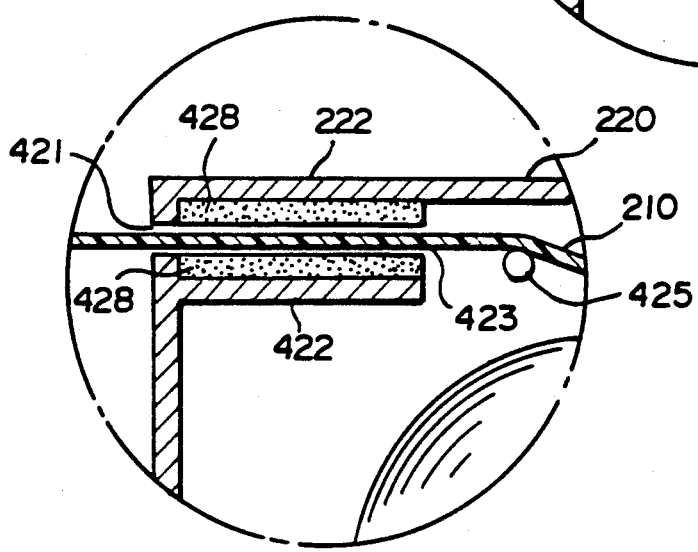

FIG. 26 shows the film outlet portion of the unused film cassette part in a still further embodiment of the second long-test-film cassette for biochemical analysis in accordance with the present invention. In this embodiment, soft foamed materials 428, 428 are provided instead of the piled materials 427, 427 in the embodiment shown in FIG. 25. Sponge, foamed styrol, foamed polyurethane or the like may be used as the soft foamed materials 428, 428.

Embodiments of the test film cassette loading system in accordance with the present invention will hereinbelow be described with reference to FIGS. 27 to 33.

Figure 27:
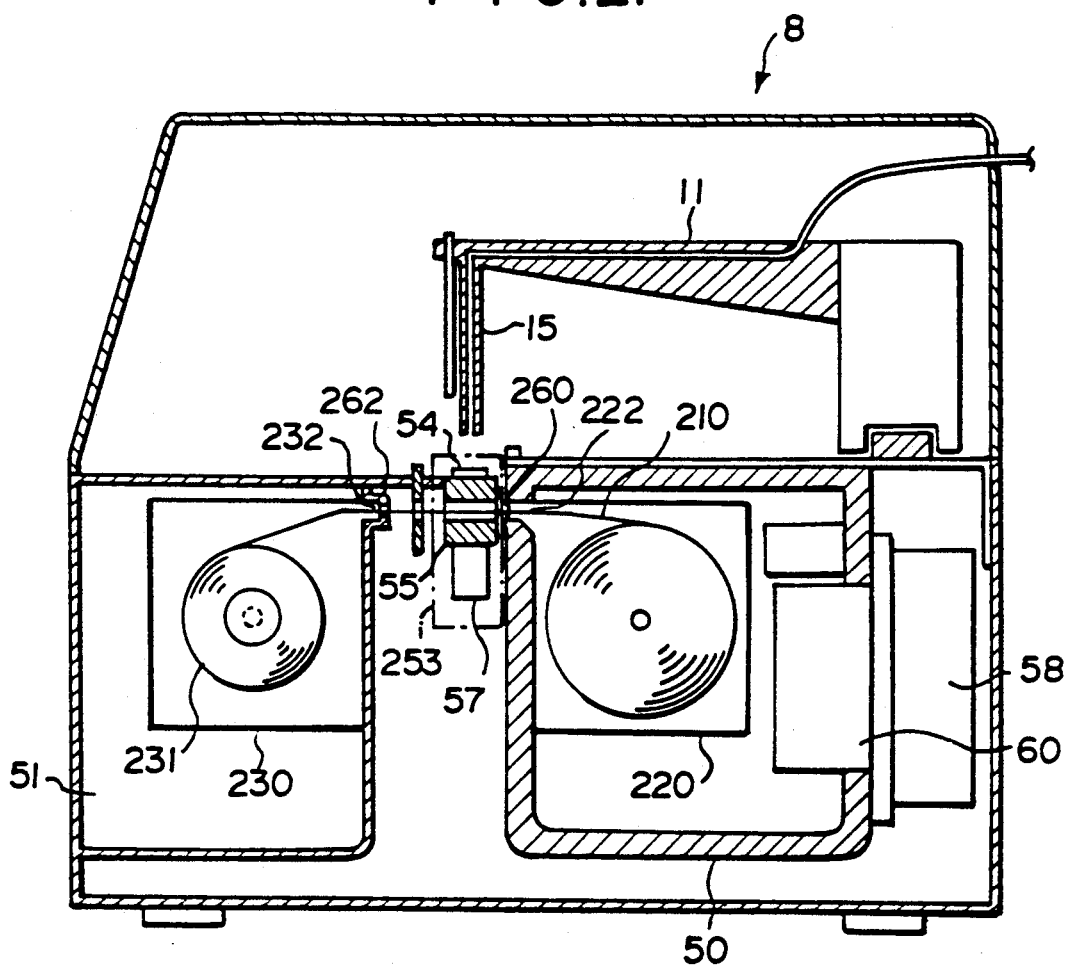
FIG. 27 is a sectional view showing an example of the colorimetric analysis apparatus whose refrigerating compartment is loaded with the unused film cassette part accommodating the unused long test film by an embodiment of the test film cassette loading system in accordance with the present invention.

FIG. 27 shows an example of the colorimetric analysis apparatus wherein the unused film cassette part accommodating the unused long test film is loaded to the refrigerating compartment by the cassette loading system in accordance with the present invention. In FIG. 27, similar elements are numbered with the same reference numerals with respect to FIG. 13.

Figure 28:
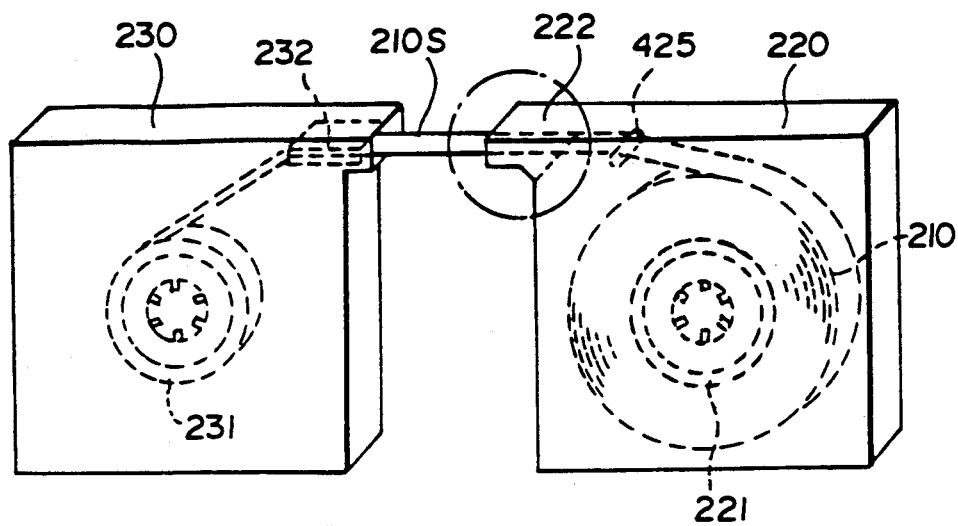
FIG. 28 is a perspective view showing an example of the long-test-film cassette for biochemical analysis which is loaded by the test film cassette loading system in accordance with the present invention.

FIG. 28 shows an example of the long-test-film cassette used in the cassette loading system in accordance with the present invention. In FIG. 28, similar elements are numbered with the same reference numerals with respect to FIG. 10. The film outlet portion 222 is protruded from the main body of the unused film cassette part 220.

Figure 29:
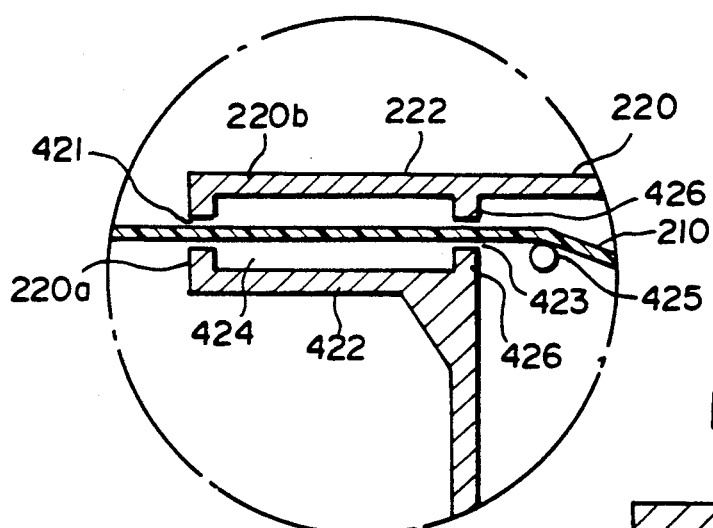
FIG. 29 is an enlarged sectional view showing an example of the configuration of the film outlet portion of the unused film cassette part in the long-test-film cassette shown in FIG. 28.

FIG. 29 shows an example of the film outlet portion 222 of the unused film cassette part 220 at the portion indicated in the circle in FIG. 28. With reference to FIG. 29, the unused film cassette part 220 is provided with the film outlet portion 222 protruded from the main body thereof, and the film outlet hole 421 is formed in the side wall 220a of the film outlet portion 222. At the film outlet portion 222, the elongated channel 424 is formed by the extension of the upper wall of the main body of the unused film cassette part 220 and the wall 422 of the film outlet portion 222.

A blocking member 426 having a film passage hole 423 of a size allowing the passage of the long test film 210 therethrough is provided on the side of the channel 424 opposite to the film outlet hole 421. A guide roller 425 for guiding the long test film 210 and making smooth the movement of the long test film 210 to the film outlet portion 222 is provided close to the film outlet portion 222. The height of the channel 424 should preferably be made small to such an extent that the movement of the long test film 210 therethrough is not obstructed, and the length of the channel 424 should preferably be made long within a range allowable in the unused film cassette part 220 accommodating the long test film 210. The blocking member 426 need not necessarily be provided, depending on the shape of the channel 424.

Figure 30:
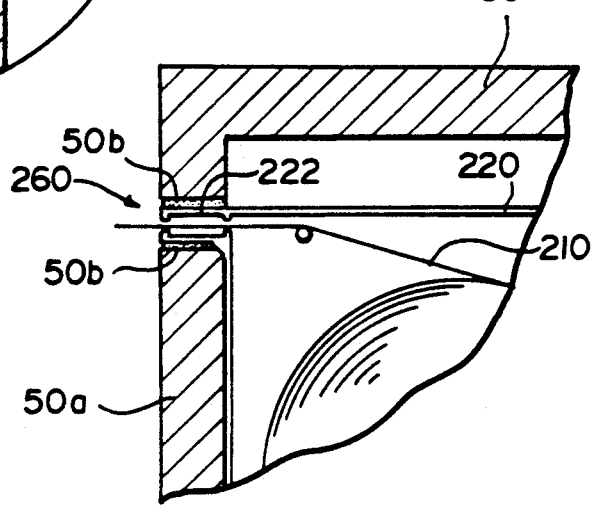
FIG. 30 is an enlarged sectional view showing the film outlet portion of the long-test-film cassette shown in FIG. 28 fitted in a film outlet hole of the refrigerating compartment.

Reverting to FIG. 27, the unused film cassette part 220 is loaded in the refrigerating compartment 50 with the film outlet portion 222 fitted into the film outlet hole 260 of the refrigerating compartment 50. FIG. 30 is an enlarged sectional view showing the region where the film outlet portion 222 is fitted in the film outlet hole 260 of the refrigerating compartment 50.

With reference to FIG. 30, the film outlet hole 260 of the refrigerating compartment 50 has a size to which the film outlet portion 222 of the unused film cassette part 220 substantially fits. Soft foamed material layers 50b, 50b constituted by sponge rubber sheets, sponge plastic sheets or the like are secured as a cushioning material to the faces of the side wall 50a of the refrigerating compartment 50 defining the film outlet hole 260. As the unused film cassette part 220 is loaded in the refrigerating compartment 50 with the film outlet portion 222 of the unused film cassette part 220 fitted in the film outlet hole 260 of the refrigerating compartment 50, no ambient air substantially enters the refrigerating compartment 50 through the film outlet hole 260 thereof, and cool air in the refrigerating compartment 50 does not leak to the exterior. The soft foamed material layers 50b, 50b may also be constituted by the piled materials as will be described with reference to FIG. 32, or may be omitted in the case where the film outlet hole 260 of the refrigerating compartment 50 is formed accurately to match the shape of the film outlet portion 222.

Figure 31:
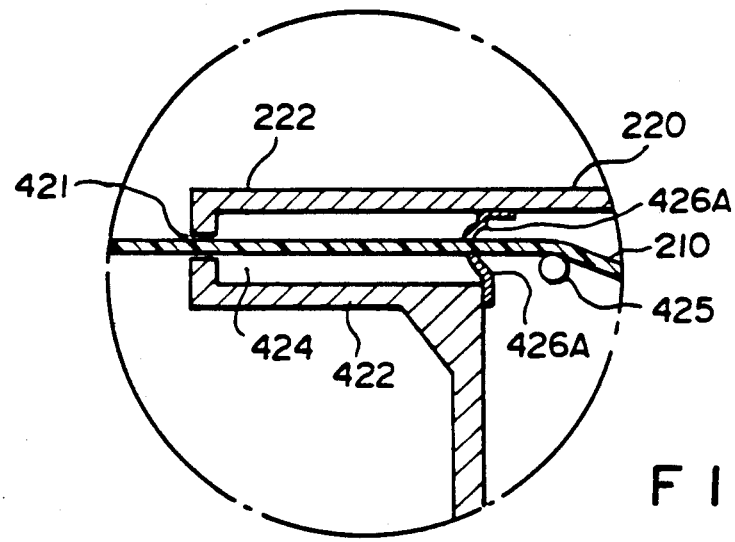
FIG. 31, 32 and 33 are enlarged sectional views showing further examples of the configurations of the film outlet portion of the unused film cassette part in the long-test-film cassette shown in FIG. 28.
Figure 32:
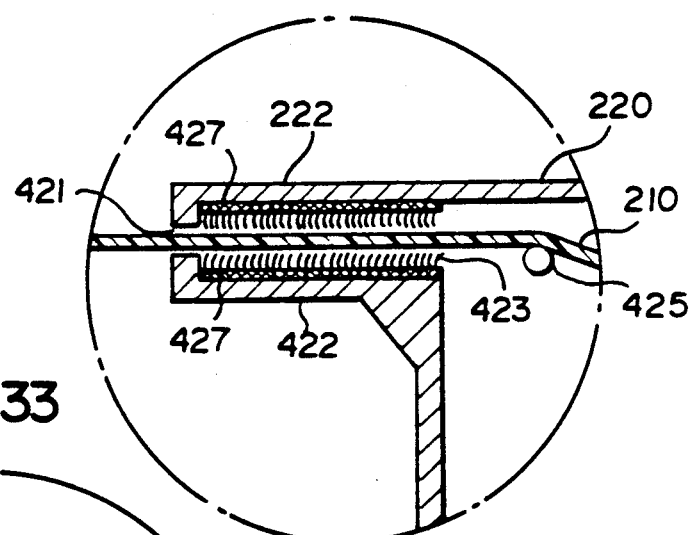
Figure 33:
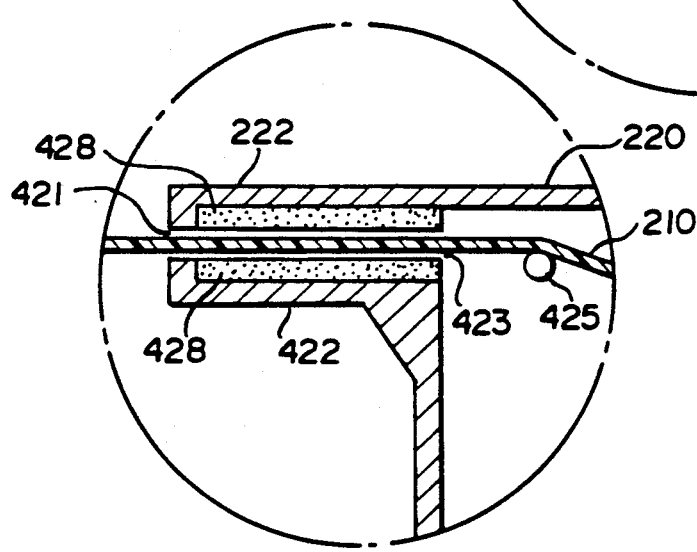

FIGS. 31 to 33 show other examples of the film outlet portion 222 of the unused film cassette part 220 at the portion indicated in the circle in FIG. 28.

With reference to FIG. 31, the configuration shown is the same as the configuration shown in FIG. 29, except that the resilient member 426A is provided instead of the blocking member 426 shown in FIG. 29. The resilient member 426A is slightly tilted inwardly toward the channel 424, and the leading edge of the resilient member 426A slightly contacts the long test film 210. The resilient member 426A should preferably be formed of a film or a sheet of rubber, a thermoplastic resin or the like. The resilient member 426A may be provided inside of the channel 424 closer to the film outlet hole, and a plurality of resilient members 426A, 426A, . . . may be provided in the channel 424.

With reference to FIG. 32, piled materials 427, 427 are provided to sandwich the long test film 210 in the channel 424 shown in FIG. 29. In this example, the blocking member 426 need not necessarily be provided. The piled materials 427, 427 may be selected from, for example, velvet, mat, velveteen, a cloth electrostatically flocked with fibers or yarns, and other known materials. Felt may also be employed for this purpose.

With reference to FIG. 33, soft foamed materials 428, 428 are provided instead of the piled materials 427, 427 in the example shown in FIG. 32. Sponge, foamed styrol, foamed polyurethane or the like may be used as the soft foamed materials 428, 428.

With the configuration wherein the film outlet portion 222 of the unused film cassette part 220 is formed as mentioned above, high-temperature, high-humidity ambient air is prevented from entering the unused film cassette part 220.

Figure 34:
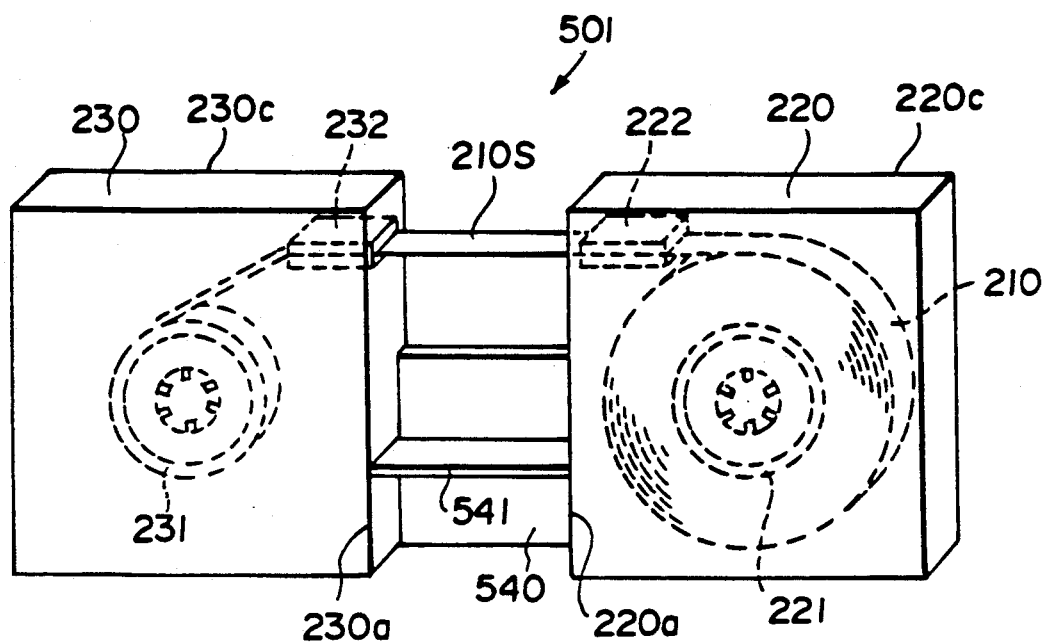
FIG. 34 is a perspective view showing an embodiment of the third long-test-film cassette for biochemical analysis in accordance with the present invention.
Figure 35:
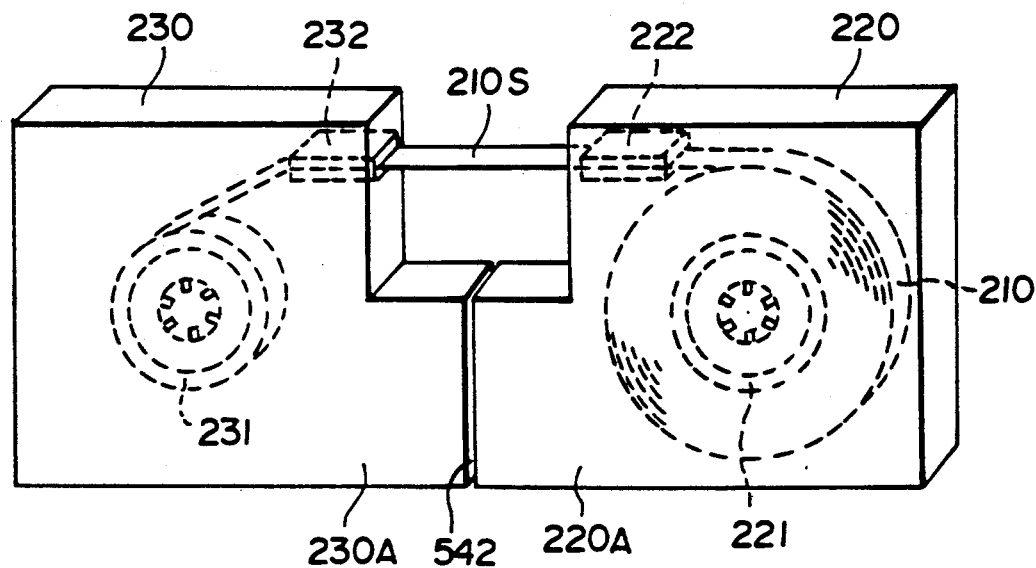
FIG. 35 is a perspective view showing another embodiment of the third long-test-film cassette for biochemical analysis in accordance with the present invention.
Figure 36:
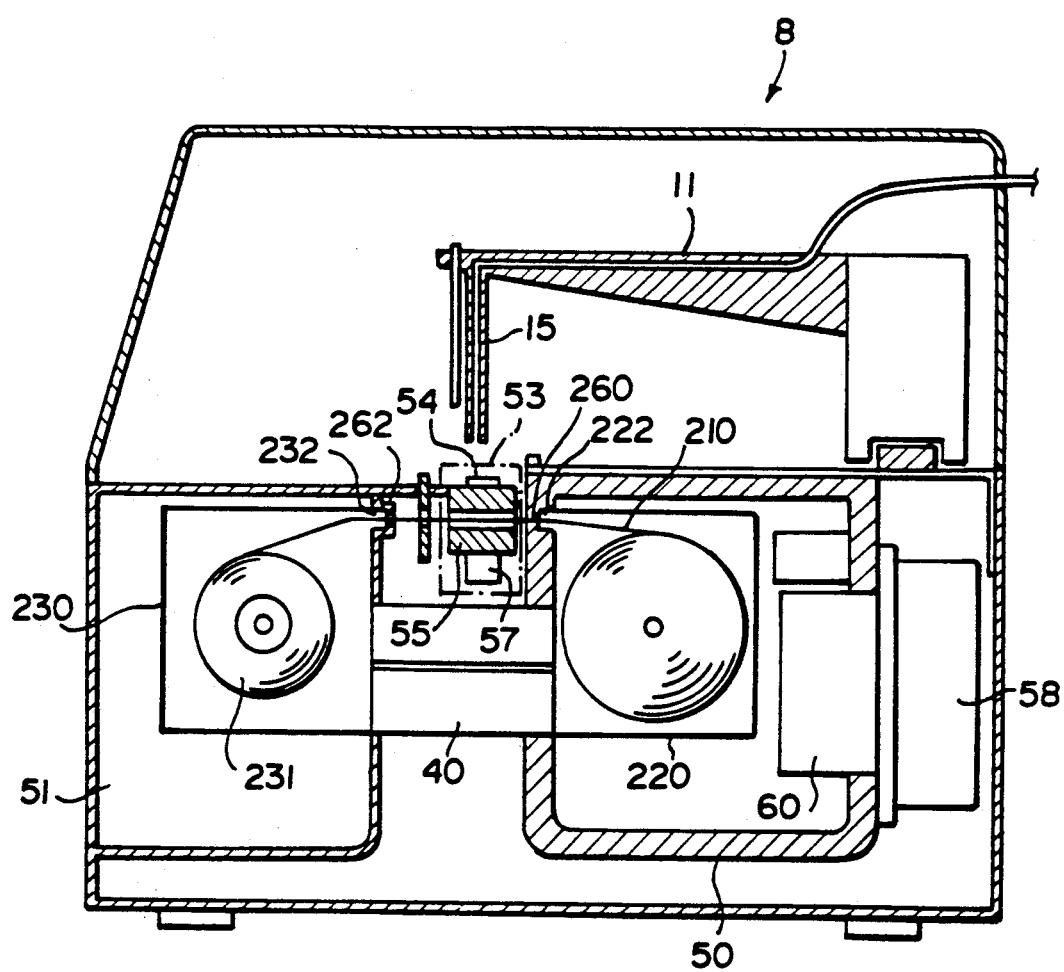
FIG. 36 is a sectional view showing an example of the colorimetric analysis apparatus wherein the third long-test-film cassette for biochemical analysis in accordance with the present invention is used.

Embodiments of the third long-test-film cassette for biochemical analysis in accordance with the present invention will hereinbelow be described with reference to FIGS. 34, 35 and 36. In FIGS. 34, 35 and 36, similar elements are numbered with the same reference numerals with respect to FIG. 10.

With reference to FIG. 34, a long-test-film cassette 501 for biochemical analysis comprises the unused film cassette part 220 and the used film cassette part 230 which are combined integrally with each other by a plate member 540 secured flush with a broader side wall 220c of the unused film cassette part 220 and a broader side wall 230c of the used film cassette part 230, and a plate-like rib 541 secured normal to the surface of the plate member 540 and normal to the surface of a narrower side wall 220a of the unused film cassette part 220 and the surface of a narrower side wall 230a of the used film cassette part 230 facing each other. Sample application, incubation and measurement are carried out at the film portion 210S of the long test film 210 exposed between the cassette parts 220 and 230. Therefore, the plate member 540 is secured only at the lower areas of the side walls 220a and 230a in FIG. 34 so that a space is formed around the film portion 210S for allowing the film portion 210S to be fitted to the analysis region of the analysis apparatus. The plate member 540 and the plate-like rib 541 may be prepared independently of the side walls 220a, 230a, 220c and 230c, and may then be secured to the corresponding side walls by adhesion, engagement, fitting and other means. Alternatively, the plate member 540 and/or the plate-like rib 541 may originally be combined integrally with the side walls by molding or the like.

FIG. 35 shows another embodiment of the third long-test-film cassette for biochemical analysis in accordance with the present invention.

The embodiment shown in FIG. 35 is the same as the embodiment shown in FIG. 34, except that the unused film cassette part 220 and the used film cassette part 230 are provided with a protrusion 220A and a protrusion 230A respectively at a part of the surfaces facing each other, and leading side walls of the protrusion 220A and the protrusion 230A are secured to each other to form a partition 542. The partition 542 may be formed by preparing the unused film cassette part 220 and the used film cassette part 230 independently of each other, and then securing the leading side walls of the protrusion 220A and the protrusion 230A to each other by adhesion, engagement, fitting or other means. Alternatively, the partition 542, the unused film cassette part 220 and the used film cassette part 230 may be prepared integrally with each other from the original step. The partition 542 may be composed of double walls with a space intervening therebetween or with a heat insulating material filled therebetween. Also, the partition 542 may be closer to one of the unused film cassette part 220 and the used film cassette part 230 than to the other thereof.

FIG. 36 shows the long-test-film cassette shown in FIG. 34 loaded to the colorimetric analysis apparatus 8. In FIG. 36, similar elements are numbered with the same reference numerals with respect to FIG. 13.

In the embodiments of the third long-test-film cassette for biochemical analysis in accordance with the present invention shown in FIGS. 34 and 35, the configurations of the film outlet portion 222 of the unused film cassette part 220 in the embodiments of the second long-test-film cassette as shown in FIGS. 22 to 26 may be employed.

Modifications of the long-test-film cassette for biochemical analysis in accordance with the present invention will hereinbelow be described with reference to FIGS. 37 to 55. These modifications are applicable to all of the aforesaid embodiments.

Figure 37:
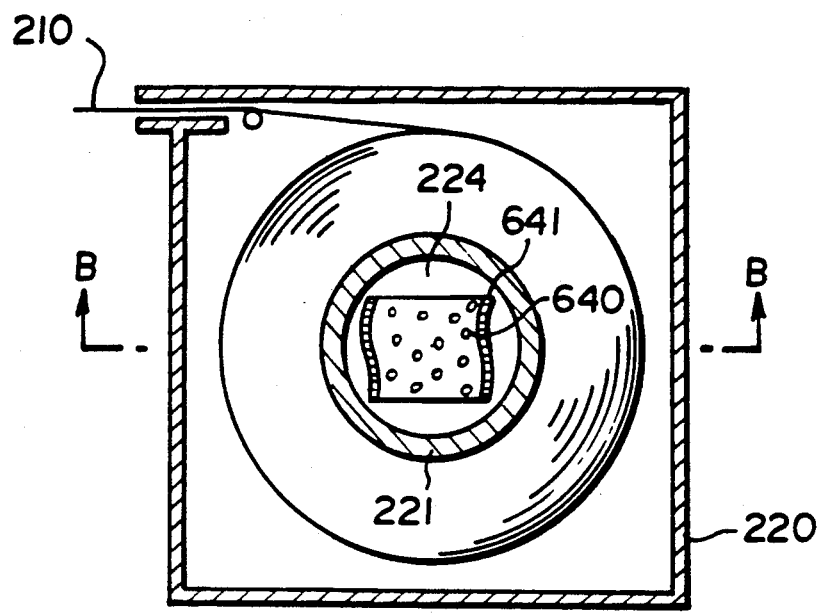
FIG. 37 is a sectional view showing an unused film cassette part in a modification of the long-test-film cassette for biochemical analysis in accordance with the present invention.
Figure 38:
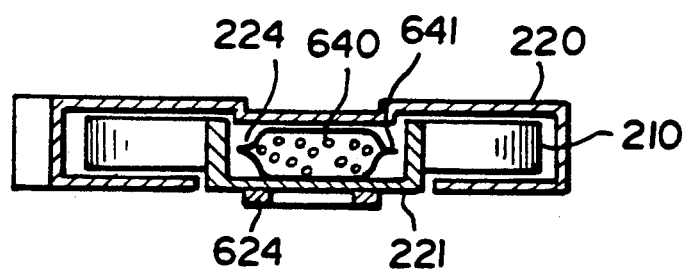
FIG. 38 is a sectional view taken along line B—B of FIG. 37.

With reference to FIGS. 37 and 38, a gas adsorbing or absorbing agent 640 is accommodated inside of the unused film cassette part 220. FIG. 37 is a sectional view showing the unused film cassette part 220, and FIG. 38 is a sectional view taken along line B—B of FIG. 37. The gas adsorbing or absorbing agent 640 is contained in a case 641 and accommodated in a hollow region 224 inside of the reel 221. An engagement member 624 for wind-up and stop of the long test film 210 is provided on the outer face of the reel 221.

The gas adsorbing or absorbing agent 640 should preferably be composed of a substance which is capable of adsorbing or absorbing gases such as steam, oxygen and ammonia having detrimental effects on the analysis performance, for example, deteriorating the analysis performance and producing errors in the analysis results, and which is non-deliquescent. The gas adsorbing or absorbing agent 640 having such properties can be selected from known substances such as silica gel, zeolite, activated carbon, and activated alumina. Though the gas adsorbing or absorbing agent 640 may be directly accommodated in the hollow region 224, it should preferably be housed in the case 641 and accommodated in this form in the hollow region 224. The case 641 may be of any shape, for example, a bag or a box, insofar as it is formed of a gas-permeable material free of deterioration by the gas adsorbing or absorbing agent, for example, a paper, a non-woven fabric, a film or a sheet having small perforations, or a film or a sheet of a foamed material having communicating pores.

The case 641 containing the gas adsorbing or absorbing agent 640 need not necessarily be accommodated in the hollow region 224 of the reel 221, and may be accommodated at a corner inside of the unused film cassette part 220.

With the modification shown in FIG. 37 wherein the gas adsorbing or absorbing agent 640 is accommodated in the unused film cassette part 220, any detrimental gas such as steam, oxygen and ammonia entering the unused film cassette part 220 can be adsorbed or absorbed by the gas adsorbing or absorbing agent 640, and no adverse effects on the long test film 210 are produced. Therefore, the analysis results can be obtained accurately and reliably.

Figure 39:
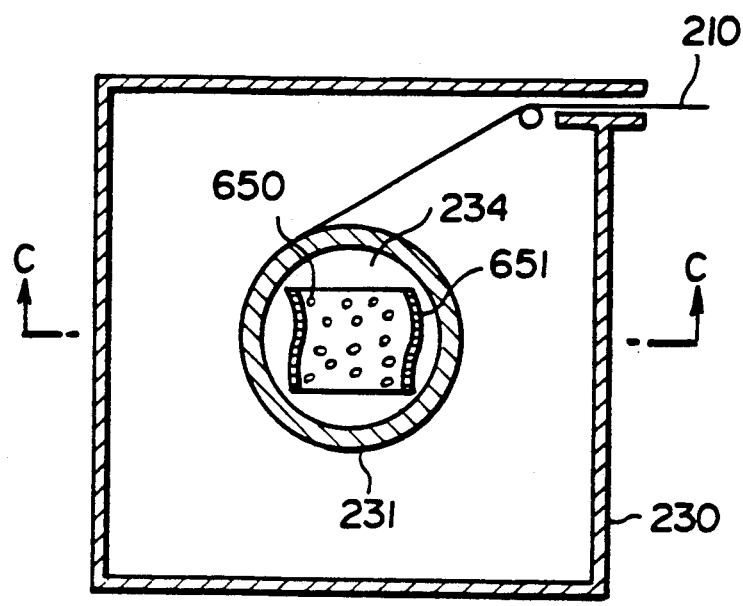
FIG. 39 is a sectional view showing a used film cassette part in another modification of the long-test-film cassette for biochemical analysis in accordance with the present invention.
Figure 40:
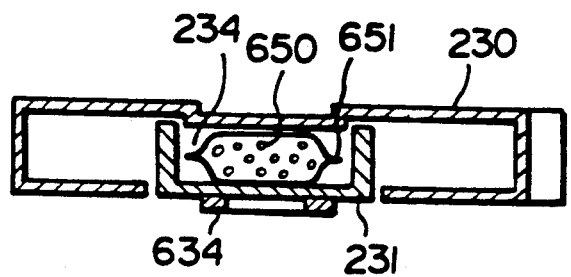
FIG. 40 is a sectional view taken along line C—C of FIG. 39.

With reference to FIGS. 39 and 40, a gas releasing agent 650 is accommodated in the used film cassette part 230. FIG. 39 is a sectional view showing the used film cassette part 230, and FIG. 40 is a sectional view taken along line C—C of FIG. 39. The gas releasing agent 650 is contained in a case 651 and accommodated in this form in a space 234 inside of the reel 231. An engagement member 634 for wind-up and stop of the long test film 210 is provided on the outer face of the reel 231.

The gas releasing agent 650 releases an antiseptic gas and/or a bactericidal gas (for example, active oxygen, active chlorine, and/or a bactericidal gas) capable of preventing or minimizing rotting of the liquid sample absorbed in the used long test film. The gas releasing agent 650 should preferably be composed of a substance capable of releasing a gas for destroying or restricting multiplication of bacteria in body fluid used as the liquid sample.

Substances having such properties are generally known as antiseptic agents, bactericidal agents, mildew-proofing agents, disinfectants and the like. The gas releasing agent 650 may be selected from such known substances.

For example, chloride of lime, sodium hypochlorite, naphthalene, cresol, creosote, or tar may be used as the gas releasing agent 650.

Though the gas releasing agent 650 may be directly accommodated in the hollow region 234, it should preferably be housed in the case 651 and accommodated in this form in the hollow region 234. The case 651 may be of any shape, for example, a bag or a box, insofar as it is formed of a gas-permeable material free of deterioration by the gas releasing agent, for example, a paper, a non-woven fabric, a film or a sheet having small perforations, or a film or a sheet of a foamed material having communicating pores. The case 651 containing the gas releasing agent 650 need not necessarily be accommodated in the hollow region 234 of the reel 231, and may be accommodated at a corner inside of the used film cassette part 230.

With the modification shown in FIG. 39 wherein the gas releasing agent 650 is accommodated inside of the used film cassette part 230, the liquid sample contained in the used long test film 210 accommodated in the used film cassette part 230 can be prevented from rotting so that no smell accompanying the rotting is produced and the analysis environment is maintained clean. Therefore, the analysis accuracy and analysis apparatus are not adversely affected, and the analysis results can be obtained accurately and reliably.

Instead of the gas releasing agent 650, a gas adsorbing or absorbing agent may be accommodated in the used film cassette part 230. In this case, the gas adsorbing or absorbing agent should preferably be composed of a substance which is capable of adsorbing or absorbing gases such as smell, steam, and ammonia produced by the liquid sample absorbed in the used long test film 210 or rotted products thereof and polluting the analysis environment and adversely affecting the analysis results, and which is non-deliquescent. The gas adsorbing or absorbing agent having such properties can be selected from known substances such as silica gel, zeolite, activated carbon, activated alumina, and deodorants.

With the modification wherein the gas adsorbing or absorbing agent is accommodated in the used film cassette part 230, any smell produced by the liquid sample applied to the used long test film 210 or rotted products thereof can be prevented from being released to the exterior of the used film cassette part 230, polluting the analysis environment, and adversely affecting the analysis accuracy and analysis apparatus. Therefore, the analysis results can be obtained accurately and reliably.

Figure 41:
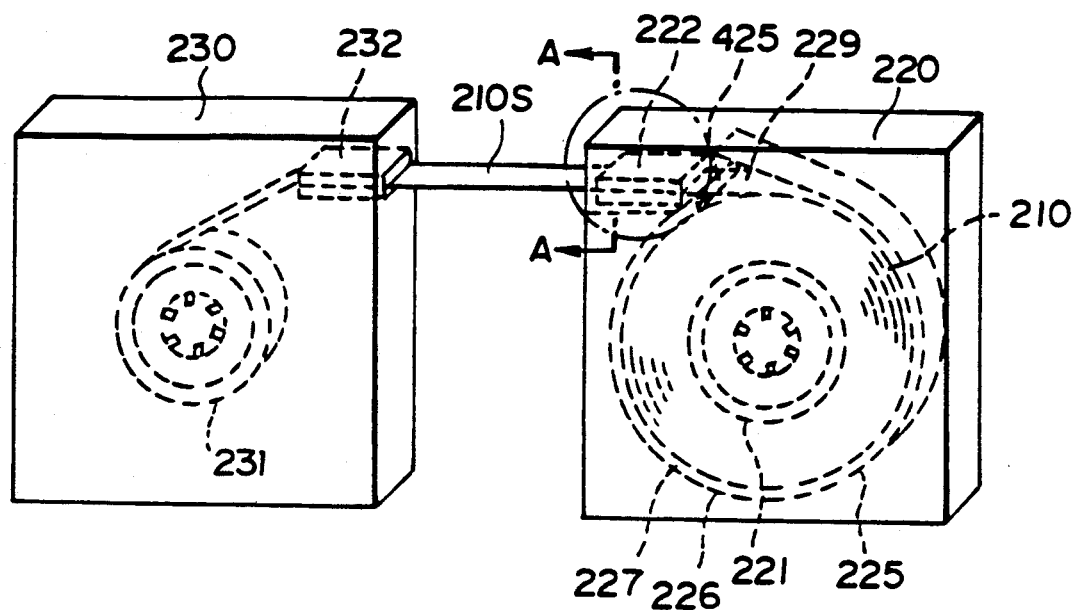
FIG. 41 is a perspective view showing a further modification of the long-test-film cassette for biochemical analysis in accordance with the present invention with an unused film cassette part and a used film cassette part spaced away from each other.

FIG. 41 shows a still further modification of the long-test-film cassette for biochemical analysis in accordance with the present invention. In FIG. 41, similar elements are numbered with the same reference numerals with respect to FIG. 10.

Figure 42:
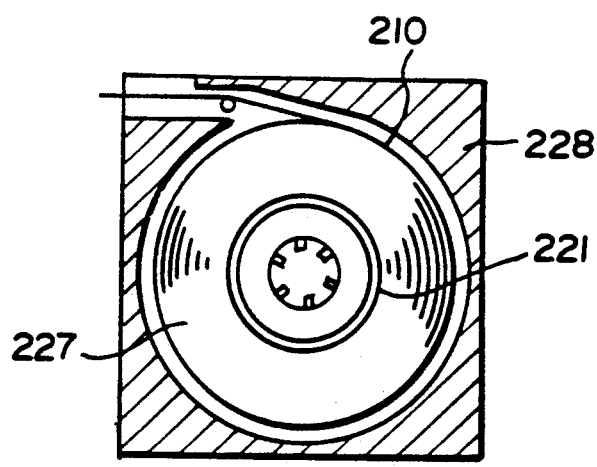
FIG. 42 is a sectional view showing an unused film cassette part in a still further modification of the long-test-film cassette for biochemical analysis in accordance with the present invention.
Figure 46:
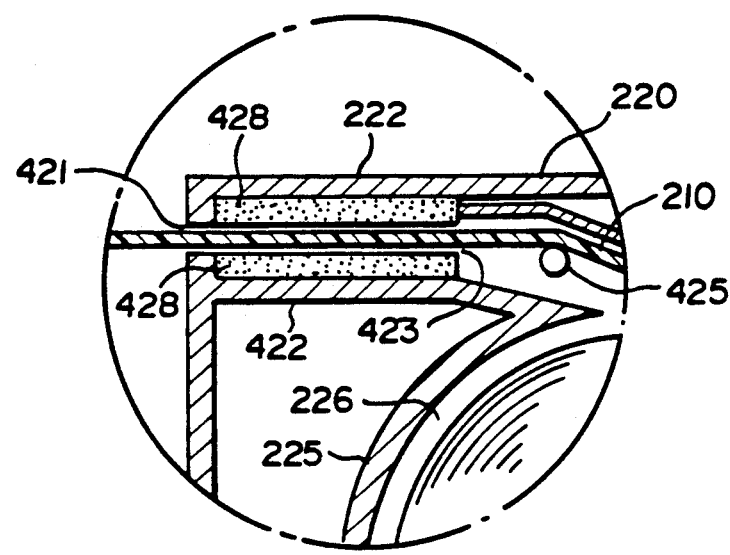

With reference to FIG. 41, the unused film cassette part 220 is provided with a partition plate 225 for defining a nearly disk-like test film accommodating region 227 slightly larger than the roll of the overall length of the long test film 210, and a path 229 for the long test film 210. The partition plate 225 should preferably be provided so that a gap 226 between the partition plate 225 and the outermost surface of the roll of the long test film 210 is as small as possible. The nearly disk-like test film accommodating region 227 and the path 229 for the long test film 210 should preferably be provided airtight so that they are open only at the film outlet. The partition plate 225 may be formed integrally with the unused film cassette part 220 at the time of the formation of the unused film cassette part 220 by molding or the like. Alternatively, the partition plate 225 may first be prepared independently of the unused film cassette part 220, and then secured to the unused film cassette part 220 by adhesion, engagement or other means. Also, as shown in FIG. 42, a filler 228 may be applied on the inner walls of the unused film cassette part 220, thereby to form the nearly disk-like test film accommodating region 227.

FIGS. 43, 44, 45 and 46 show the modifications wherein the configurations of the film outlet portion 222 of the unused film cassette part 220 as shown in FIGS. 22, 24, 25 and 26 are employed in the configuration shown in FIG. 41. In FIGS. 43, 44, 45 and 46, similar elements are numbered with the same reference numerals with respect to FIGS. 22, 24, 25 and 26.

With the modifications shown in FIGS. 41 to 46 wherein the test film accommodating region 227 of the unused film cassette part 220 is provided in a nearly disk-like shape slightly larger than the roll of the long test film 210 so that the unused portion of the long test film 210 contacts less air, the unused portion of the long test film 210 accommodated in the unused film cassette part 220 can be maintained at a low temperature and low humidity capable of substantially eliminating moisture absorption of the unused film portion even though the long-test-film cassette which has been stored at a low temperature and low humidity up to the time of use is processed in ordinary ambient air for loading to the refrigerating compartment of the analysis apparatus (the processing time is comparatively short). Therefore, the long test film 210 does not deteriorate, and analysis results can be obtained accurately with good reproducibility.

Figure 47:
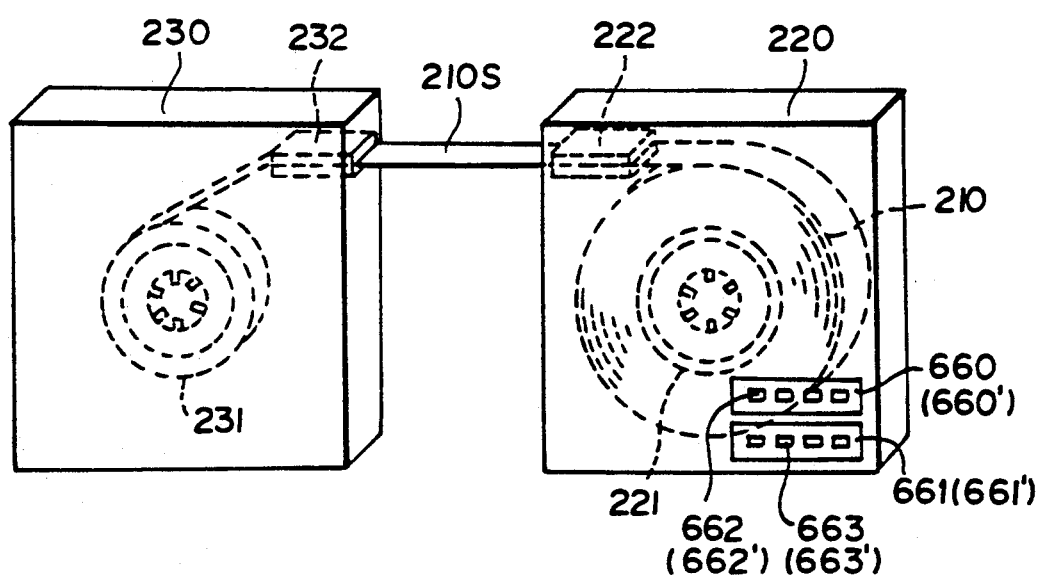
FIG. 47 is a perspective view showing another modification of the long-test-film cassette for biochemical analysis in accordance with the present invention.

FIG. 47 shows a modification wherein an irreversible temperature indicating label 660 and an irreversible humidity indicating label 661 are provided on the outer surface of the unused film cassette part 220.

By way of example, a label indicating the maximum value of the temperatures of the environment to which the label has been exposed, a label indicating the cumulative elapsed time of exposure thereof to the environment at a temperature above a specific critical value, or a label indicating both of these items can be employed as the irreversible temperature indicating label 660. As such a label, Monitor Label supplied by 3M Company or the like may be used. With the label indicating the maximum value of the temperatures of the environment to which the label has been exposed, the maximum value of the temperatures of the environment to which the long-test-film cassette has already been exposed can be investigated even though the ambient temperature at the time of processing of the long-test-film cassette is equal to a predetermined temperature, and it is possible to accurately judge whether the long test film 210 is or is not usable for analysis. With the label indicating the cumulative elapsed time of exposure thereof to the environment at a temperature above a specific critical value, it is possible to investigate how long the long-test-film cassette has been exposed to the temperature above the specific critical value and to more accurately judge whether the long test film 210 is or is not usable for analysis. In the case where two or more labels whose critical temperature values are different from each other are used, the temperature range of the environment to which the long-test-film cassette has been exposed can also be investigated. With the aforesaid labels, the maximum temperature and the cumulative elapsed time can be discriminated based on, for example, a produced color or a change in color indicated at a display window 662.

On the other hand, by way of example, a label indicating the maximum value of the humidity of the environment to which the label has been exposed, a label indicating the cumulative elapsed time of exposure thereof to the environment at humidity above a specific critical value, or a label indicating both of these items can be employed as the irreversible humidity indicating label 661. As such a label, a label having silica gel encapsulated therein or the like may be used. The irreversible humidity indicating label 661 is utilized in the same manner as the irreversible temperature indicating label 660, except that humidity is investigated by means of a display window 663.

The indicating labels 660 and 661 can be selected from the known labels, and may be provided at any position on the outer surface of the unused film cassette part 220 by, for example, adhesion with or without use of an adhesive tape, or engagement. Since the indicating labels 660 and 661 are irreversible, they should be provided on the outer surface of the unused film cassette part 220 or activated after the unused film cassette part 220 is placed in the environment having a temperature and humidity not higher than predetermined values.

With the modification shown in FIG. 47 wherein the outer surface of the unused film cassette part 220 is provided with the irreversible temperature indicating label 660 and/or the irreversible humidity indicating label 661, the temperature and/or humidity history of the environment to which the long-test-film cassette for biochemical analysis has been exposed during the storage prior to the use for analysis or between interruption of analysis and reuse can be recognized readily. Therefore, it is possible to eliminate the problem that a long-test-film cassette deteriorated and giving incorrect analysis results is used erroneously for analysis.

In FIG. 47, instead of the irreversible temperature indicating label 660 and the irreversible humidity indicating label 661, a reversible temperature indicating label 660' and a reversible humidity indicating label 661' may be provided on the outer surface of the unused film cassette part 220.

Any label having a display area 662' for indicating the current temperature of the environment to which the label is being exposed can be used as the reversible temperature indicating label 660'. For this purpose, it is possible to use, for example, a label having a plurality of materials exhibiting changes in color above and below a predetermined temperature, a label (such as a liquid crystal label) forming different colors in different predetermined temperature ranges, or a label provided with a means for indicating different symbols such as numerals in different predetermined temperature ranges. Such changes in the label 660' must be reversible, and should occur as quickly as possible in accordance with changes in temperature of the environment. A single label may be used for this purpose, or two or more labels of different indicating system may be used in combination.

Also, as for the reversible humidity indicating label 661', any label can be employed insofar as it is provided with a display area 663' for indicating the current humidity of the environment to which the label is being exposed. The reversible humidity indicating label 661' is utilized in the same manner as the reversible temperature indicating label 660', except that humidity is investigated by means of the display area 663'.

With the modification wherein the outer surface of the unused film cassette part 220 is provided with the reversible temperature indicating label 660' and/or the reversible humidity indicating label 661', the current temperature and/or humidity of the environment to which the long-test-film cassette for biochemical analysis loaded in the refrigerating compartment is being exposed can be readily recognized visually or by means of a color sensor during processing of the cassette for storage, movement and analysis operations. Therefore, an action for adjusting the environmental conditions to appropriate values can be taken quickly, and it is possible to eliminate the problem that a long-test-film cassette deteriorated and giving incorrect analysis results is used erroneously for analysis.

Figure 48:
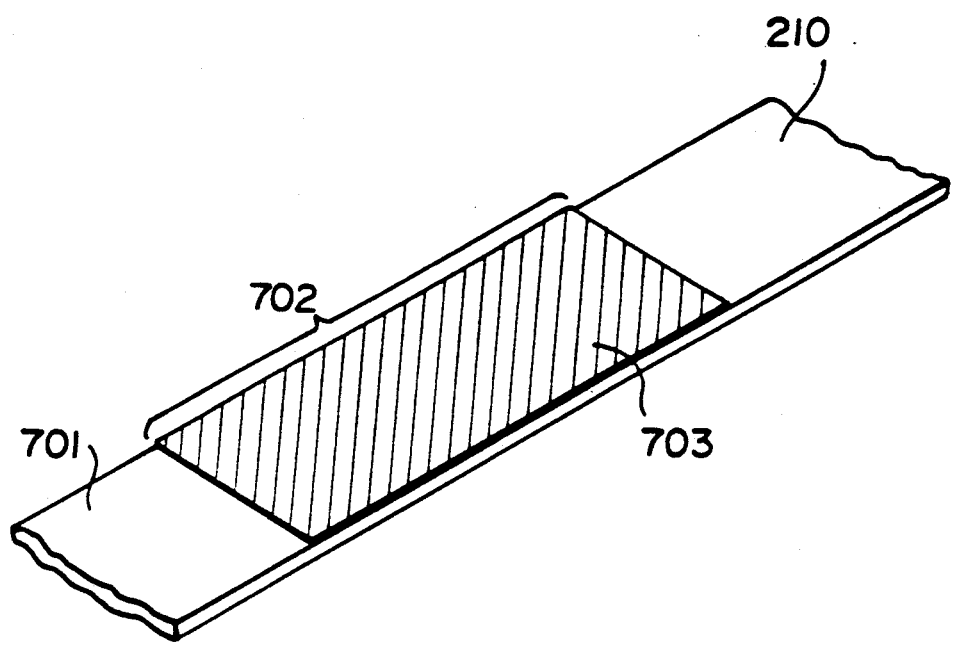
FIGS. 48, 49, 50, 51 and 52 are schematic views showing the examples of the recording regions of leader tapes in further modifications of the long-test-film cassette for biochemical analysis in accordance with the present invention.

FIG. 48 shows another modification wherein a leader tape 701 having a recording region 702 on which information on the long test film 210 is recorded is connected with the leading edge of the long test film 210 disposed as shown in FIG. 10. The leader tape 701 is pulled out of the aforesaid film outlet portion 222 of the unused film cassette part 220 shown in FIG. 10, and introduced from the aforesaid film inlet portion 232 into the used film cassette part 230. The leading edge of the leader tape 701 is secured to the reel 231 in the used film cassette part 230. The recording region 702 is accommodated in the unused film cassette part 220 prior to the use of the long test film 210 for analysis. When analysis is to be begun, the recording region 702 is pulled out of the unused film cassette part 220, the information recorded on the recording region 702 is read by an information reading means (not shown) between the unused film cassette part 220 and the used film cassette part 230, and the analysis method and/or analysis conditions are adjusted based on the read information. Thereafter, the long test film 210 is pulled out of the unused film cassette part 220, and sample application, incubation and measurement are carried out between the unused film cassette part 220 and the used film cassette part 230. The width of the leader tape 701 should preferably be nearly equal to the width of the long test film 210.

The recording region 702 may be of any type insofar as the information on the long test film 210 including at least one item among, for example, the analysis object, analysis method, analysis conditions, number of analysis operations and lot number can be discriminated visually, mechanically, optically, magnetically or electrically.

In FIG. 48, the leader tape 701 is made of the same material as the support 211 of the long test film 210 shown in FIG. 11A, and a magnetic recording layer 703 is overlaid on the leader tape 701 to constitute the recording region 702. The magnetic recording layer 703 can be formed by the technique known for a magnetic recording medium such as an audio tape. The magnetic recording layer 703 may be overlaid on the lower surface of the leader tape 701, and may be provided over a part of the width of the leader tape 701. The long test film 210 and the leader tape 701 may be prepared independently at the original step, and may then be connected with each other by adhesion. Also, the leader tape 701 and the recording region 702 may be prepared independently at the original step, and may then be connected with each other by adhesion. The method of recording the information on the magnetic recording layer 703 is not limited to a particular one, and any known method may be employed for this purpose.

Figure 49:
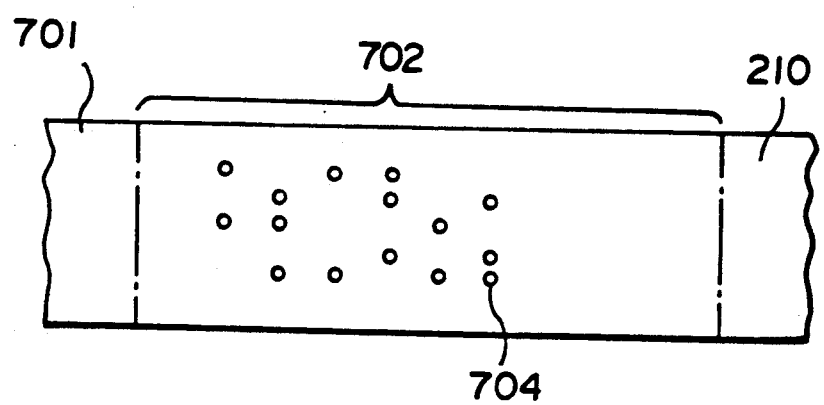

FIG. 49 shows the leader tape 701 provided with the recording region 702 having an indicating means composed of holes. In FIG. 49, holes 704 indicating the information on the long test film 210 are provided in the recording region 702 of the leader tape 701. The system of a paper tape (or a punched tape) used as an input and output means of a computer may be utilized as the indicating system with the holes 704. The holes 704 may be provided in the leader tape 701 itself. Alternatively, a paper sheet or a film of other material may be overlaid on the surface of the leader tape 701 or joined between the long test film 210 and the leader tape 701, and the holes 704 may be provided in the paper sheet or the film of other material. Connection of the leader tape 701 with the long test film 210 and the like are the same as mentioned with reference to FIG. 48.

Figure 50:
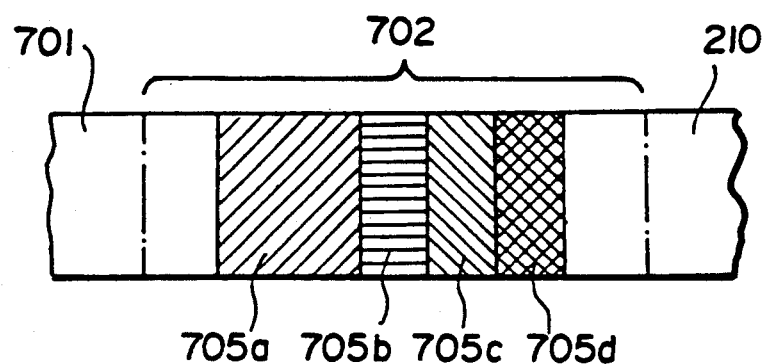

FIG. 50 shows the leader tape 701 provided with the recording region 702 having an indicating means based on colors. With reference to FIG. 50, the recording region 702 of the leader tape 701 is provided with color areas 705a, 705b, 705c and 705d indicating the information on the long test film 210. A wide range of information on the long test film 210 can be recorded by combinations of the number, size, shape, color tone, color density and the like of the color areas. The recording region 702 may be provided on the front or rear surface of the leader tape 701. The recording region 702 may be provided on the leader tape 701 itself. Alternatively, a paper sheet or a film of other material may be overlaid on the surface of the leader tape 701 or joined between the long test film 210 and the leader tape 701, and the recording region 702 may be provided on the paper sheet or the film of other material. Connection of the leader tape 701 with the long test film 210 and the like are the same as mentioned with reference to FIG. 48.

Figure 51:
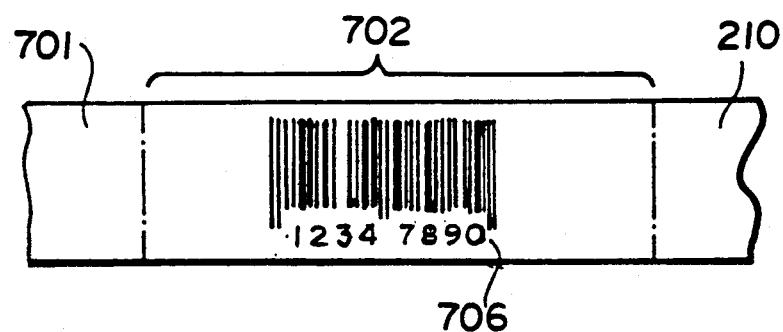

FIG. 51 shows the leader tape 701 provided with the recording region 702 having an indicating means comprising bar codes. With reference to FIG. 51, the recording region 702 of the leader tape 701 is provided with bar codes 706 indicating the information on the long test film 210. The system of information recording by bar codes is already known, and a wide range of information on the long test film 210 can be recorded by such system. The manner of provision of the recording region 702 on the leader tape 701 is the same as mentioned with reference to FIG. 50. Connection of the leader tape 701 with the long test film 210 and the like are the same as mentioned with reference to FIG. 48.

Figure 52:
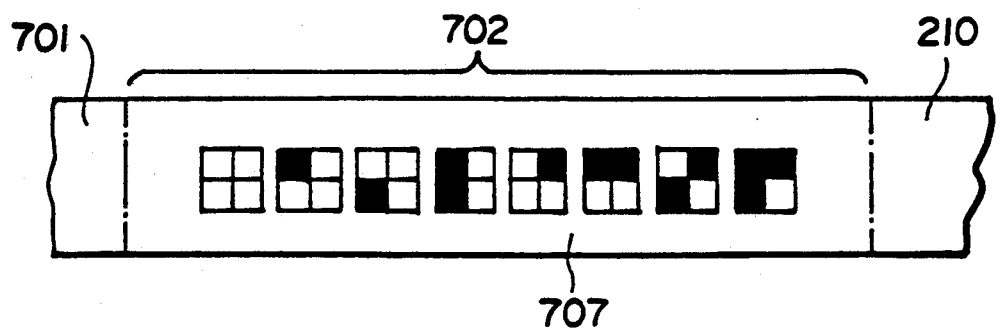

FIG. 52 shows the leader tape 701 provided with the recording region 702 having an indicating means comprising "□" shaped codes. With reference to FIG. 52, the recording region 702 of the leader tape 701 is provided with "□" shaped codes 707 indicating the information on the long test film 210. The system of information recording by the "□" shaped codes is already known, and a wide range of information on the long test film 210 can be recorded by such system. The manner of provision of the recording region 702 on the leader tape 701 is the same as mentioned with reference to FIG. 50. Connection of the leader tape 701 with the long test film 210 and the like are the same as mentioned with reference to FIG. 48.

The information reading means may be selected in accordance with the type of the recording region 702. For example, a magnetic head may be used for reading the magnetically recorded information, or an optical reading means may be used for reading the color areas, holes, bar codes and "□" shaped codes. The information reading means may be provided, for example, between the film outlet hole 260 of the refrigerating compartment 50 and the analysis region 253 shown in FIG. 13, or between the analysis region 253 and the wind-up compartment 51 shown in FIG. 13. Also, in the case where the optical reading means is employed as the information reading means, the measuring device 57 shown in FIG. 13 may be utilized as the optical reading means.

The information on the long test film 210 read by the information reading means may be displayed by an appropriate means, and the analysis operations can be carried out based on the displayed information. Also, based on the information, the analysis method and analysis conditions can be adjusted automatically, and the analysis apparatus can be operated automatically.

With the modifications shown in FIGS. 48 to 52, the kind of the long-test-film cassette for biochemical analysis can be discriminated visually. Also, after the cassette is loaded to the analysis apparatus, it is possible for the analysis apparatus to discriminate the kind of the long test film 210, display the information on the long test film 210 recorded on the recording region 702, and issue a warning with respect to erroneous cassette loading. Therefore, the kind and condition of the long test film 210 loaded in the analysis apparatus can be investigated prior to analysis, erroneous analysis operations can be prevented, and the analysis method, the analysis conditions and the like can be adjusted automatically based on the information. Therefore, analysis can be carried out quickly, automatically and sequentially.

Modifications wherein both side faces of the long test film 210 are protected by a substantially moisture-impermeable material will hereinbelow be described with reference to FIGS. 53, 54 and 55.

The long test film 210 has a markedly wider area at the flat surface regions than at the side faces as shown in FIG. 11A, and it is considered that adverse effects of ambient moisture occur mainly at the flat surface regions. However, the long test film 210 is wound in the roll form. Therefore, the flat surface regions of the long test film 210 are protected by the long test film 210 itself in the rolled condition and are not readily affected by ambient moisture, and the side faces of the long test film 210 entirely exposed to the exterior will be readily affected by ambient moisture. In general, a wide film web is first prepared, and then cut into the long test film 210. Also, as mentioned above with reference to FIG. 11A, the long test film 210 has the configuration permeable to moisture. Therefore, even though the area of the side faces of the long test film 210 is small, when the side faces contact wet ambient air, moisture readily permeates from the side faces into the overall long test film 210 and deteriorates it.

Figure 53:
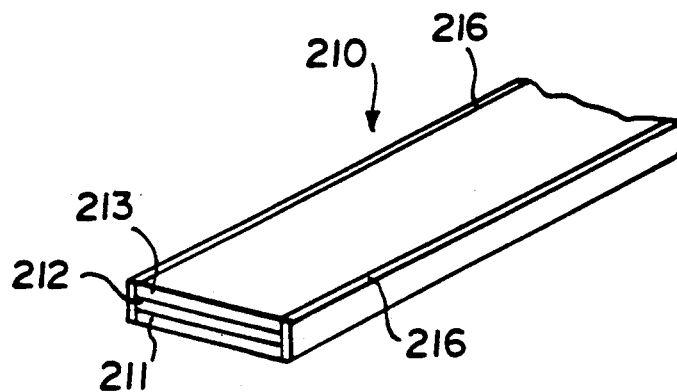
FIGS. 53, 54 and 55 are perspective views showing examples of the long test films in still further modifications of the long-test-film cassette for biochemical analysis in accordance with the present invention.

To eliminate the aforesaid problem, in the modification shown in FIG. 53, moisture-impermeable covering layers 216, 216 are provided on both side faces of the long test film 210. The covering layers 216, 216 should preferably be formed of a hydrophobic material selected from the group consisting of rubber, thermoplastic resins and thermosetting resins. Though any of known hydrophobic materials may be employed, the covering layers 216, 216 should more preferably be formed by applying an adhesive prepared from one of the aforesaid materials. The thicknesses of the covering layers 216, 216 may be such that natural moisture absorption of the long test film 210 is prevented, and may be selected in accordance with the material used.

Figure 54:
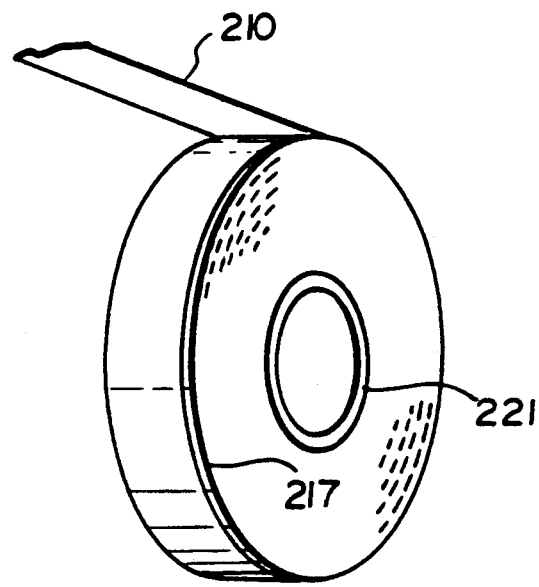

With reference to FIG. 54, the long test film 210 is wound up around the reel 221 to form a roll, and covering layers 217, 217 are provided on the ring-like regions on both side faces of the roll. The covering layers 217, 217 should preferably be composed of the hydrophobic material as mentioned above, and should more preferably be formed by applying an adhesive prepared from the aforesaid material. Since the long test film 210 is in the rolled, laminated form, the side faces thereof are joined together by the covering layers 217, 217. As the long test film 210 is unwound from the roll with the roll rotating when the long test film 210 is to be used for analysis, the adhesion strength of the covering layers 217, 217 should not be so high. Even though the adhesion strength of the covering layers 217, 217 is low, natural moisture absorption at both side faces of the long test film 210 can be prevented substantially. The thicknesses of the covering layers 217, 217 may be selected in accordance with the kind of the material constituting the covering layers 217, 217.

The covering layers 217, 217 may be constituted by films or sheets made of the aforesaid hydrophobic material. In this case, the covering layers 217, 217 should preferably be adhered to the ring-like regions of the roll of the long test film 210 by an adhesive. As would be understood from the foregoing, the adhesive should preferably has a low strength. The thicknesses of the films or the sheets may be very thin insofar as natural moisture permeation can be prevented. Also, in the case where the covering layers 217, 217 have comparatively large thicknesses and are adhered by the adhesive, the adhesive need not necessarily be applied over the overall ring-like areas, and may be applied pointwise or linearly.

Figure 55:
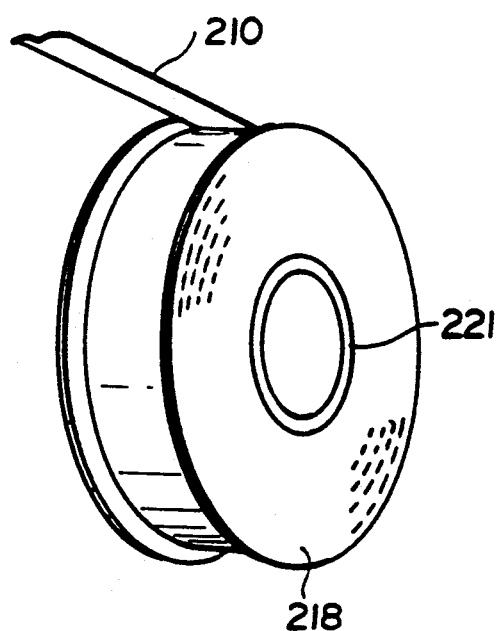

With reference to FIG. 55, the reel 221 around which the long test film 210 is wound up in the roll form is provided with ring-like plates 218, 218 contacting at least the ring-like regions on both side faces of the roll of the long test film 210 and having sizes covering the ring-like regions. The ring-like plates 218, 218 may be formed of rubber, a thermoplastic resin, a paper, a thermosetting resin laminated plate, a metal or other materials. The ring-like plates 218, 218 may originally be formed integrally with the reel 221. Alternatively, the ring-like plates 218, 218 may first be prepared independently of the reel 221, and may then be secured to the reel 221 by adhesion, engagement or fitting. The long test film 210 is wound up around the reel 221, and both side faces of the long test film 210 contact the ring-like plates 218, 218. Therefore, the side faces of the long test film 210 are prevented from moisture absorption.

With the modifications shown in FIG. 53, 54 and 55 wherein both side faces of the long test film 210 are protected impermeably to moisture, no moisture is absorbed from the side faces. Also, since the long test film 210 is wound up in the roll form, no moisture is absorbed from the flat surface region. Therefore, even though the long-test-film cassette which has been stored at a low temperature and low humidity up to use for analysis is processed in ordinary ambient air for loading to the analysis apparatus, the long test film 210 in the unused film cassette part 220 can be substantially prevented from moisture absorption and maintained at low humidity. Accordingly, the analysis results can be obtained accurately with good reproducibility.

We claim:

1. A long-test-film, biochemical analysis cassette for biochemical analysis of a sample liquid, said biochemical analysis cassette comprising:
   i) an unused film cassette part accommodating an unused long test film which contains a reagent for biochemical analysis, and
   ii) a used film cassette part provided independent of and separate from said unused film cassette part for accommodating said long test film which has been pulled out of said unused film cassette part and used for biochemical analysis,
   wherein said long test film is exposed at a portion between said used film cassette part and said unused film cassette part such that said used and unused film cassette parts are horizontally spaced from each other by the exposed portion of said long test film at least when said sample liquid is applied thereto and incubated therewith.

2. A long-test-film, biochemical analysis cassette for biochemical analysis of a sample liquid as defined in claim 1 wherein said unused film cassette part accommodates said unused long test film for biochemical analysis in a roll form, said used film cassette part winds up and accommodates said used film in a roll form, a leading edge of said film is secured to a reel in said used film cassette part, and further comprising means, separate from said film, for readily releasably joining said unused film cassette part and said used film cassette part to each other.

3. A long-test-film, biochemical analysis cassette for biochemical analysis of a sample liquid as defined in claim 1 wherein said unused film cassette part accommodates said unused long test film for biochemical analysis in a roll form, said used film cassette part winds up and accommodates said used film in a roll form, a leading edge of said film is secured to a reel in said used film cassette part, and said unused film cassette part and said used film cassette part are packed in a single container so that said film does not twist nor move so much.

4. A long-test-film, biochemical analysis cassette for biochemical analysis of a sample liquid as defined in claim 3 wherein said container is construct so as to seal said long test film cassette against ambient air.

5. A long-test-film, biochemical analysis cassette for biochemical analysis of sample liquid as defined in claim 1 wherein said unused film cassette part accommodates said unused long test film for biochemical analysis in a roll form, said used film cassette parts winds up and accommodates said used film in a roll form, a leading edge of said film is secured to a reel in said used film cassette part, and a gas adsorbing or absorbing agent is accommodated in said unused film cassette part.

6. A long-test-film, biochemical analysis cassette for biochemical analysis of a sample liquid as defined in claims 2, 3 or 5 wherein said long test film for biochemical analysis is provided with a multi-layer analysis element comprising at least a layer through which a liquid sample to be analyzed is spread, a reagent layer and a light-permeable support.

7. A long-test-film, biochemical analysis cassette for biochemical analysis of a sample liquid as defined in claim 5 wherein said gas adsorbing or absorbing agent is constructed so as to adsorb or absorb a gas selected from the group consisting of steam, oxygen and ammonia, and is non-deliquescent.

8. A long-test-film, biochemical analysis cassette for biochemical analysis of a sample liquid as defined in claim 7 wherein said gas adsorbing or absorbing agent is selected from the group consisting of silica gel, zeolite, activated carbon, and activated alumina.

9. A long-test-film, biochemical analysis cassette for biochemical analysis of a sample liquid as defined in claim 5 wherein said gas adsorbing or absorbing agent is accommodated in a gas-permeable case and is accommodated in this form in said unused film cassette part.

10. A long-test-film, biochemical analysis cassette for biochemical analysis of a sample liquid, said biochemical analysis cassette comprising:
i) an unused film cassette part accommodating an unused long test film which contains a reagent for biochemical analysis in a roll form, and
ii) a used film cassette part, which is separate and distinct from said unused film cassette part, for winding up and accommodating the used film, which has been used for biochemical analysis, in a roll form, a leading edge of said film being secured to a reel in said used film cassette part,
wherein a test film outlet portion of said unused film cassette part has such a configuration that air inside of said unused film cassette part and air outside thereof do not substantially mix with each other naturally, and
wherein said long test film is exposed at a portion between said used film cassette part and said unused film cassette part such that said used and unused film cassette parts are horizontally spaced from each other by the exposed portion of said long test film at least when said sample liquid is applied thereto and incubated therewith.

11. A long-test-film, biochemical analysis cassette for biochemical analysis of a sample liquid as defined in claim 10 wherein said long test film for biochemical analysis is provided with a multi-layer analysis element comprising at least a layer through which a liquid sample to be analyzed is spread, a reagent layer and a light-permeable support.

12. A long-test-film, biochemical analysis cassette for biochemical analysis of a sample liquid as defined in claim 10 wherein said test film outlet portion of said unused film cassette part includes an elongated channel constructed so as to allow movement of said film therethrough.

13. A long-test film, biochemical analysis cassette for biochemical analysis of a sample liquid as defined in claim 12 wherein a piled material is disposed in said channel.

14. A long-test film, biochemical analysis cassette for biochemical analysis of a sample liquid as defined in claim 12 wherein a soft foamed material is disposed in said channel.

15. A long-test-film, biochemical analysis cassette for biochemical analysis of a sample liquid, said biochemical analysis cassette comprising:
i) an unused film cassette part accommodating an unused long test film which contains a reagent for biochemical analysis in a roll form, and
ii) a used film cassette part for winding up and accommodating the used film, which has been used for biochemical analysis, in a roll form,
wherein said unused film cassette part and said used film cassette part are combined integrally with each other so that the space inside of said unused film cassette part and the space inside of said used film cassette part are independent of each other, and a leading edge of said film is secured to a reel in said used film cassette part, and
wherein said long test film is exposed at a portion between said used film cassette part and said unused film cassette part such that said used and unused film cassette parts are horizontally spaced from each other by the exposed portion of said long test film at least when said sample liquid is applied thereto and incubated therewith, and
wherein said unused film cassette part and said used film cassette part are joined integrally with each other by a plate-like member, said plate-like member being adhered by an adhesive to lower side faces of said unused film cassette part and said used film cassette part, respectively, below the exposed portion of said long test film.

16. A long-test-film, biochemical analysis cassette for biochemical analysis of a sample liquid as defined in claim 15 wherein said long test film for biochemical analysis comprises a multi-layer analysis element comprising at least a layer through which a liquid sample to be analyzed is spread, a reagent layer and a light-permeable support.

17. A long-test-film, biochemical analysis cassette for biochemical analysis of a sample liquid as defined in claim 15 wherein a gas adsorbing or absorbing agent is accommodated in said unused film cassette part.

18. A long-test-film, biochemical analysis cassette for biochemical analysis of a sample liquid as defined in claim 15 wherein said gas adsorbing or absorbing agent is constructed so as to adsorb or absorb a gas selected from the group consisting of steam, oxygen and ammonia, and is non-deliquescent.

19. A long-test-film, biochemical analysis cassette for biochemical analysis of a sample liquid as defined in claim 18 wherein said gas adsorbing or absorbing agent is selected from the group consisting of silica gel, zeolite, activated carbon, and activated alumina.

20. A long-test-film, biochemical analysis cassette for biochemical analysis of a sample liquid as defined in claim 17 wherein said gas adsorbing or absorbing agent is accommodated in a gas-permeable case and is accommodated in this form in said unused film cassette part.

21. A long-test-film, biochemical analysis cassette for biochemical analysis of a sample liquid as defined in claim 1 wherein said used film cassette part and said unused film cassette part are constructed and arranged so as to be manually movable apart from each other and toward each other by pulling out or winding up, respectively, said long test film therein, such that the exposed portion of said long test film between said used film cassette part and said unused film cassette part is variable in length.

22. A long-test-film, biochemical analysis cassette for biochemical analysis of a sample liquid as defined in claim 10 wherein said used film cassette part and said unused film cassette part are constructed and arranged so as to be manually movable apart from each other and toward each other by pulling out or winding up, respectively, said long test film therein, such that the exposed portion of said long test film between said used film cassette part and said unused film cassette part is variable in length.

* * * * *

UNITED STATES PATENT AND TRADEMARK OFFICE
CERTIFICATE OF CORRECTION

PATENT NO. : 5,077,010

DATED : December 31, 1991

INVENTOR(S) : Hideo Ishizaka et al.

It is certified that error appears in the above-identified patent and that said Letters Patent is hereby corrected as shown below:

Col. 39, line 26, change "construct" to --constructed--.

Signed and Sealed this

Fifteenth Day of June, 1993

Attest:

MICHAEL K. KIRK

Attesting Officer

Acting Commissioner of Patents and Trademarks